United States Patent
Strang et al.

(10) Patent No.: US 12,295,578 B2
(45) Date of Patent: May 13, 2025

(54) ADJUNCTS FOR USE WITH SURGICAL STAPLING INSTRUMENTS

(71) Applicant: Cilag GmbH International, Zug (CH)

(72) Inventors: Heather B. Strang, West Chester, OH (US); Jordan B. Wong, Cincinnati, OH (US); Frederick E. Shelton, IV, Hillsboro, OH (US); Michael J. Vendely, Lebanon, OH (US); Taylor W. Aronhalt, Loveland, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,820

(22) Filed: Oct. 13, 2023

(65) Prior Publication Data

US 2025/0120719 A1    Apr. 17, 2025

(51) Int. Cl.
*A61B 17/072*    (2006.01)

(52) U.S. Cl.
CPC .............. *A61B 17/07292* (2013.01); *A61B 2017/07264* (2013.01); *A61B 2017/07271* (2013.01)

(58) Field of Classification Search
CPC ................................................ A61B 17/07292
See application file for complete search history.

(56) References Cited

U.S. PATENT DOCUMENTS

| | | |
|---|---|---|
| 5,403,312 A | 4/1995 | Yates et al. |
| 5,485,947 A | 1/1996 | Olson et al. |
| 6,978,921 B2 | 12/2005 | Shelton, IV et al. |
| 7,000,818 B2 | 2/2006 | Shelton, IV et al. |
| 7,401,721 B2 | 7/2008 | Holsten et al. |
| 7,407,075 B2 | 8/2008 | Holsten et al. |
| 7,422,139 B2 | 9/2008 | Shelton, IV et al. |
| 7,464,849 B2 | 12/2008 | Shelton, IV et al. |
| 7,669,746 B2 | 3/2010 | Shelton, IV |
| 7,670,334 B2 | 3/2010 | Hueil et al. |
| 7,735,703 B2 | 6/2010 | Morgan et al. |
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,123,100 B2 | 2/2012 | Holsten et al. |
| 8,141,762 B2 | 3/2012 | Bedi et al. |
| 8,210,411 B2 | 7/2012 | Yates et al. |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Food and Drug Administration 510(k) Premarket Notification, https://www.accessdata.fda.gov/scripts/crdh/cfdocs/cfpmn/pmn.cfm?ID=K182476, last update: Jan. 8, 2024, 1 page.

*Primary Examiner* — Nathaniel C Chukwurah

(57) ABSTRACT

An adjunct for use with a surgical stapling system is disclosed. The adjunct comprises a first region. The first region comprises a first composition. The adjunct comprises a second region. The second region is distal to the first region and comprises a second composition. The adjunct comprises a third region. The third region is distal to the second region. The third region comprises a third composition. The second composition differs from the first composition and the third composition.

20 Claims, 12 Drawing Sheets

(56) References Cited

U.S. PATENT DOCUMENTS

| | | |
|---|---|---|
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,499,992 B2 | 8/2013 | Whitman et al. |
| 8,540,133 B2 | 9/2013 | Bedi et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,864,007 B2 | 10/2014 | Widenhouse et al. |
| 8,876,857 B2 | 11/2014 | Burbank |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,131,940 B2 | 9/2015 | Huitema et al. |
| 9,345,481 B2 | 5/2016 | Hall et al. |
| 9,386,988 B2 | 7/2016 | Baxter, III et al. |
| 9,629,631 B2 | 4/2017 | Nicholas et al. |
| 9,770,245 B2 | 9/2017 | Swayze et al. |
| 9,788,835 B2 | 10/2017 | Morgan et al. |
| 9,839,420 B2 | 12/2017 | Shelton, IV et al. |
| 9,844,369 B2 | 12/2017 | Huitema et al. |
| 9,924,944 B2 | 3/2018 | Shelton, IV et al. |
| 10,085,749 B2 | 10/2018 | Cappola et al. |
| 10,105,142 B2 | 10/2018 | Baxter, III et al. |
| 10,123,798 B2 | 11/2018 | Baxter, III et al. |
| 10,130,363 B2 | 11/2018 | Huitema et al. |
| 10,166,023 B2 | 1/2019 | Vendely et al. |
| 10,213,203 B2 | 2/2019 | Swayze et al. |
| 10,299,792 B2 | 5/2019 | Huitema et al. |
| 10,349,939 B2 | 7/2019 | Shelton, IV et al. |
| 10,357,252 B2 | 7/2019 | Harris et al. |
| 10,517,593 B2 | 12/2019 | Gupta et al. |
| 10,537,324 B2 | 1/2020 | Shelton, IV et al. |
| 10,542,981 B2 | 1/2020 | Miller et al. |
| 10,568,624 B2 | 2/2020 | Shelton, IV et al. |
| 10,588,623 B2 | 3/2020 | Schmid et al. |
| 10,765,427 B2 | 9/2020 | Shelton, IV et al. |
| 10,898,183 B2 | 1/2021 | Shelton, IV et al. |
| 10,898,191 B2 | 1/2021 | Huitema et al. |
| 10,945,727 B2 | 3/2021 | Shelton, IV et al. |
| 10,952,724 B2 | 3/2021 | Shelton, IV et al. |
| 11,045,191 B2 | 6/2021 | Shelton, IV et al. |
| 11,058,426 B2 | 7/2021 | Nalagatla et al. |
| D933,220 S | 10/2021 | Tate et al. |
| 11,147,552 B2 | 10/2021 | Burbank et al. |
| 11,207,065 B2 | 12/2021 | Harris et al. |
| 11,229,433 B2 | 1/2022 | Schings et al. |
| 11,234,698 B2 | 2/2022 | Shelton, IV et al. |
| 11,234,700 B2 | 2/2022 | Ragosta et al. |
| 11,291,445 B2 | 4/2022 | Shelton, IV et al. |
| 11,298,129 B2 | 4/2022 | Bakos et al. |
| 11,337,693 B2 | 5/2022 | Hess et al. |
| 11,364,029 B2 | 6/2022 | Burbank et al. |
| 11,382,627 B2 | 7/2022 | Huitema et al. |
| D967,421 S | 10/2022 | Shelton, IV et al. |
| 11,490,890 B2 | 11/2022 | Harris et al. |
| 11,517,315 B2 | 12/2022 | Huitema et al. |
| D974,560 S | 1/2023 | Shelton, IV et al. |
| 11,540,826 B2 | 1/2023 | Nalagatla et al. |
| 11,571,213 B2 | 2/2023 | Huitema et al. |
| 11,589,865 B2 | 2/2023 | Shelton, IV et al. |
| 11,701,114 B2 | 7/2023 | Shelton, IV et al. |
| 11,737,752 B2 | 8/2023 | Schings et al. |
| 11,766,257 B2 | 9/2023 | Shelton, IV et al. |
| 11,826,047 B2 | 11/2023 | Huang et al. |
| 2007/0175955 A1 | 8/2007 | Shelton et al. |
| 2014/0001231 A1 | 1/2014 | Shelton, IV et al. |
| 2014/0263552 A1 | 9/2014 | Hall et al. |
| 2015/0134077 A1 | 5/2015 | Shelton, IV et al. |
| 2015/0297199 A1 | 10/2015 | Nicholas et al. |
| 2016/0095596 A1 | 4/2016 | Scirica et al. |
| 2017/0086845 A1* | 3/2017 | Vendely .............. A61B 17/0644 |
| 2017/0119387 A1* | 5/2017 | Dalessandro ....... B29C 65/4805 |
| 2017/0319205 A1 | 11/2017 | Beardsley |
| 2017/0367695 A1 | 12/2017 | Shelton, IV et al. |
| 2018/0132849 A1 | 5/2018 | Miller et al. |
| 2018/0168615 A1 | 6/2018 | Shelton, IV et al. |
| 2018/0273597 A1* | 9/2018 | Stimson ............... A61K 38/212 |
| 2019/0105047 A1 | 4/2019 | Nalagatla et al. |
| 2019/0298350 A1 | 10/2019 | Shelton, IV et al. |
| 2020/0352571 A1* | 11/2020 | Hodgkinson .... A61B 17/07292 |
| 2022/0031320 A1 | 2/2022 | Hall et al. |
| 2022/0031351 A1 | 2/2022 | Moubarak et al. |
| 2022/0047256 A1 | 2/2022 | Miller et al. |
| 2022/0047265 A1 | 2/2022 | Miller et al. |
| 2022/0304679 A1 | 9/2022 | Bakos et al. |
| 2022/0304680 A1 | 9/2022 | Shelton, IV et al. |
| 2022/0346858 A1 | 11/2022 | Aronhalt et al. |
| 2023/0119119 A1 | 4/2023 | Moubarak |

FOREIGN PATENT DOCUMENTS

| | | |
|---|---|---|
| CN | 105997173 A | 10/2016 |
| CN | 106036848 A | 10/2016 |
| CN | 108542454 A | 9/2018 |
| CN | 111195142 A | 5/2020 |

* cited by examiner

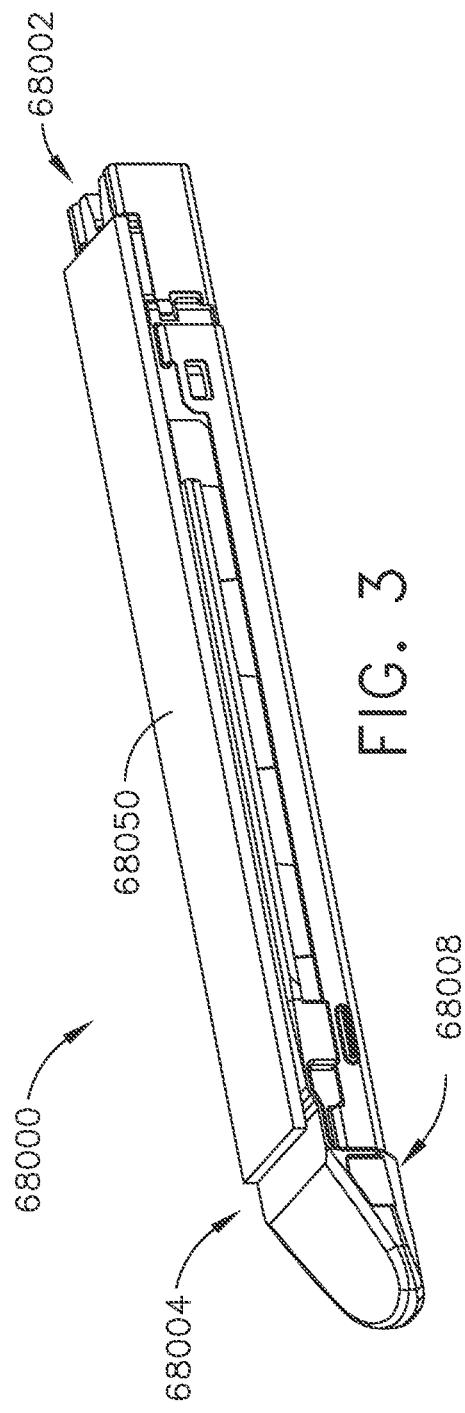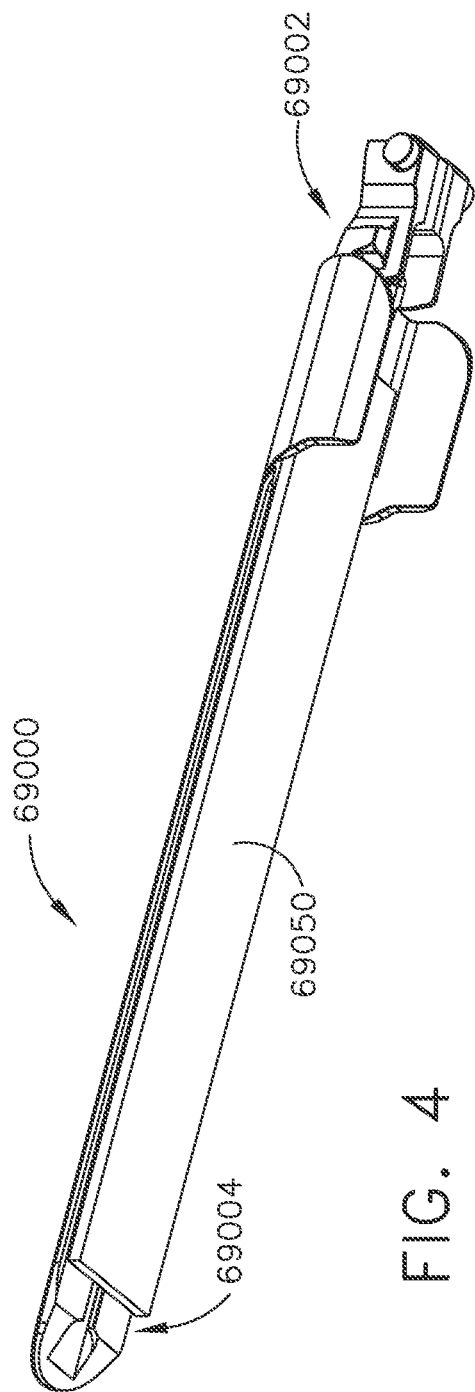

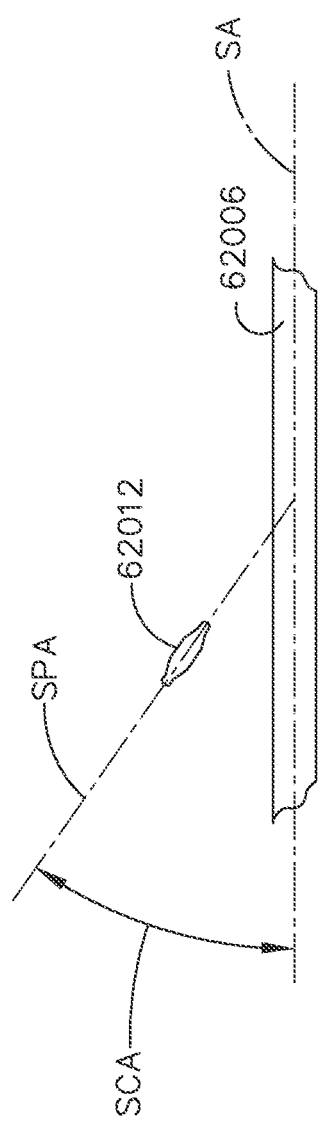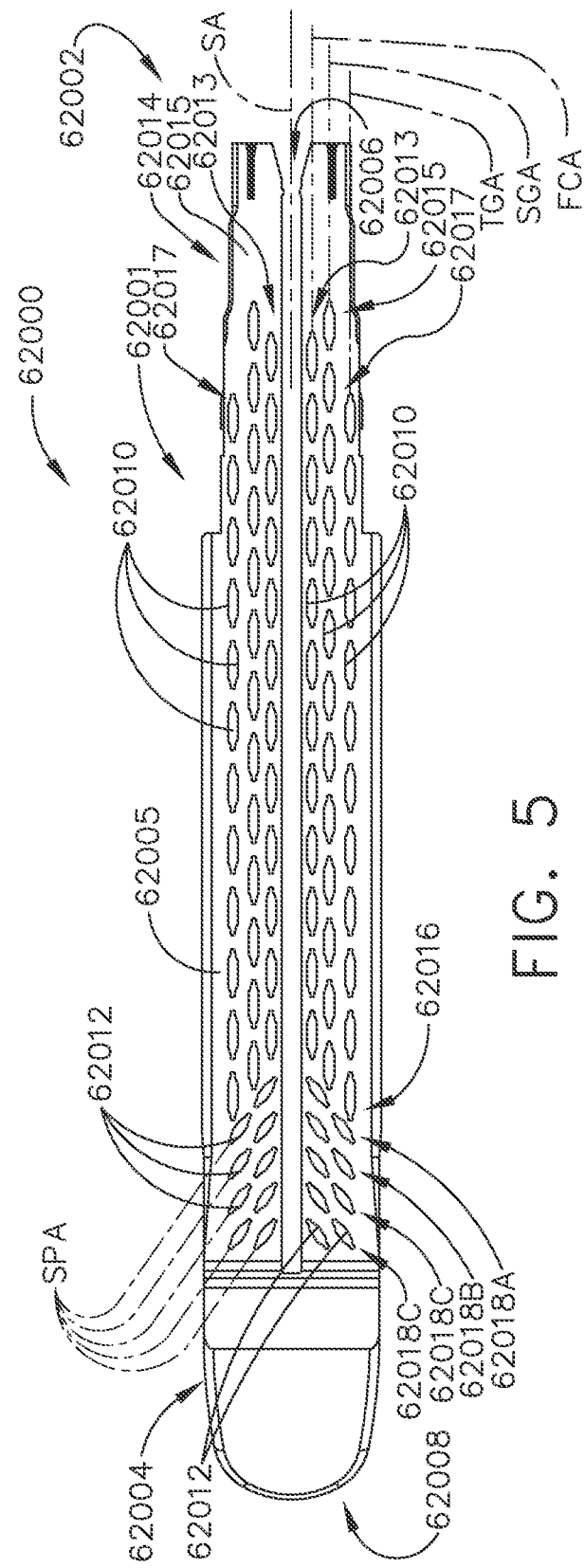

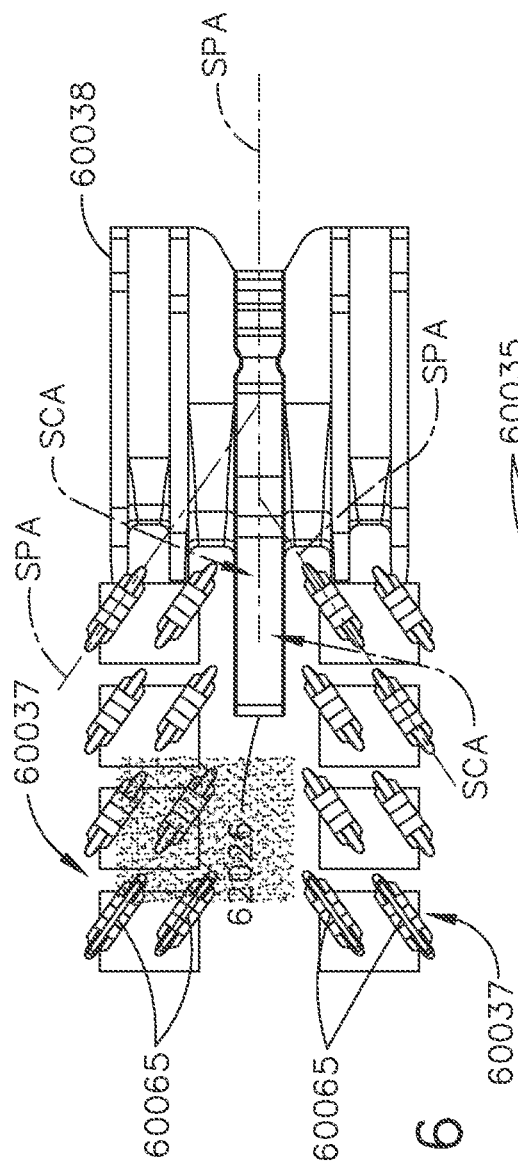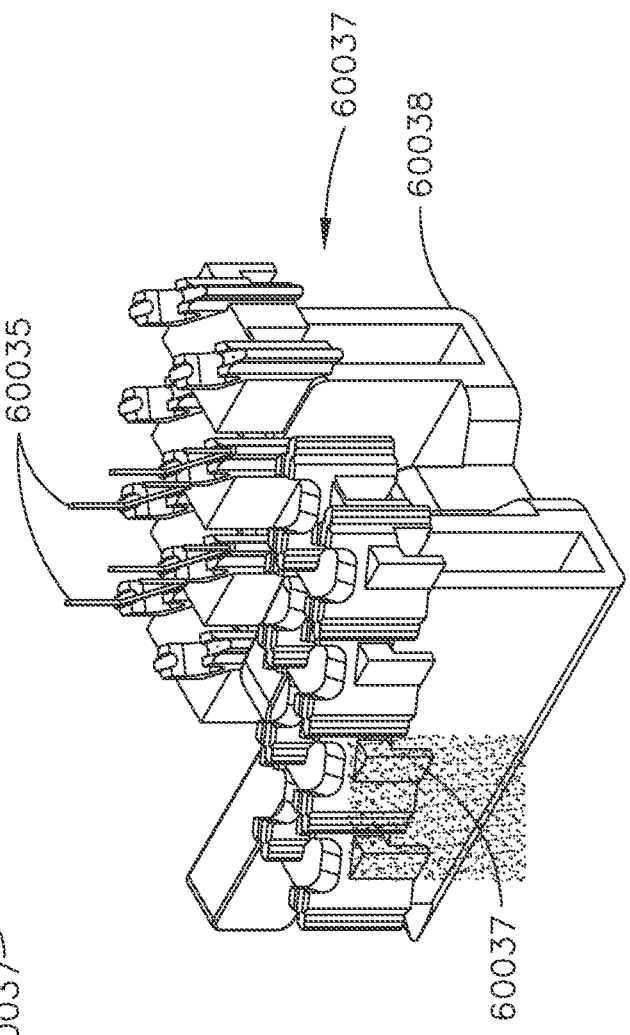

ADJUNCTS FOR USE WITH SURGICAL STAPLING INSTRUMENTS

BACKGROUND

The present invention relates to surgical instruments and, in various arrangements, to adjuncts and staple cartridges for use with surgical stapling and cutting instruments that are designed to staple and cut tissue.

Often times when using surgical stapling and cutting instruments, it is beneficial to use adjuncts in combination with the staple cartridge, the anvil, or both in order to provide support to the tissue surrounding the cut line. However, various issues can arise when using adjuncts while sequentially firing multiple staple cartridges along a single tissue cut line. For example, during deployment of a first adjunct associated with a first staple cartridge during the first of more than one firing motion, the first adjunct and staples from the first staple cartridge provide ample reinforcement along the tissue cut line at a particular location. As staples are released from a second staple cartridge comprising a second adjunct right after the first firing motion, often times, the second adjunct overlaps the first adjunct. The overlap of the second adjunct and the first adjunct provides an increased level of reinforcement along the tissue cut line at a given location.

During the stapling of the second adjunct, this level of increased reinforcement may cause the knife of the stapling instrument to drive the second adjunct distally, which is sometimes referred to as plowing. When the knife drives the second adjunct distally, the staples being fired from the second staple cartridge can be distorted during formation. As such, the staples being fired are formed improperly which can lead to bleeding and other complications during the stapling and cutting process. The present disclosure provides for improvements and modifications which minimize the distortion of staples during deployment and provide for increased efficiency and ease while transecting overlapping adjuncts.

SUMMARY

An adjunct for use with a surgical stapling system is disclosed. The adjunct comprises a first region. The first region comprises a first composition. The adjunct comprises a second region. The second region is distal to the first region and comprises a second composition. The adjunct comprises a third region. The third region is distal to the second region. The third region comprises a third composition. The second composition differs from the first composition and the third composition.

An adjunct for use with a surgical stapling system is disclosed. The adjunct comprises an elongate body comprising a proximal end, a distal end, and two lateral sides extending between the proximal end and the distal end. The elongate body further comprises a first material extending longitudinally through a central portion of the elongate body between the proximal end and the distal end. The first material comprises a first composition. The elongate body also comprises a length of second material extending longitudinally from the proximal end to the distal end between the first material and one of the lateral sides. The second material comprises a second composition that differs from the first composition. The elongate body also comprises another length of the second material extending longitudinally from the proximal end to the distal end between the first material and another one of the lateral sides.

A surgical stapling system is disclosed. The surgical stapling system comprises a staple cartridge. The staple cartridge comprises a cartridge body defining a proximal end and a distal end and an elongate slot extending from the proximal end toward the distal end, wherein the elongate slot defines a slot axis. The staple cartridge also comprises a plurality of first staple cavities aligned in three lines of first staple cavities on each side of the elongate slot. Each line of first staple cavities is aligned on a corresponding first cavity axis that is parallel to the slot axis. Each line of first staple cavities extends from the proximal end of the cartridge body to a position that is proximal to the distal end of the cartridge body. Each first staple cavity removably stores a corresponding first staple therein. The staple cartridge also comprises a plurality of second staple cavities formed on each side of the elongate slot in a distal portion of the cartridge body between the position that is proximal to the distal end and the distal end. Each second staple cavity is oriented on a second cavity axis that is arranged at angle relative to the slot axis. Each second cavity removably stores a corresponding second staple therein.

BRIEF DESCRIPTION OF THE DRAWINGS

Various features of the embodiments described herein, together with advantages thereof, may be understood in accordance with the following description taken in conjunction with the accompanying drawings as follows:

FIG. 3 is perspective view of an adjunct supported on a deck of a staple cartridge;

FIG. 4 is a perspective view of an adjunct supported adjacent to a staple-forming undersurface of an anvil of a surgical stapler;

FIG. 5 is a top view of a staple cartridge for use with a surgical instrument in accordance with the present disclosure;

FIG. 5A is a diagrammatic view of a second staple cavity in relation to a portion of a longitudinal slot of the staple cartridge of FIG. 5;

FIG. 6 is a top view of a sled, staple drivers, and staples corresponding to the second staple cavities of the staple cartridge of FIG. 5;

FIG. 7 is a perspective view of the sled, staple drivers, and staples of FIG. 6;

Corresponding reference characters indicate corresponding parts throughout the several views.

DETAILED DESCRIPTION

Figure 1:
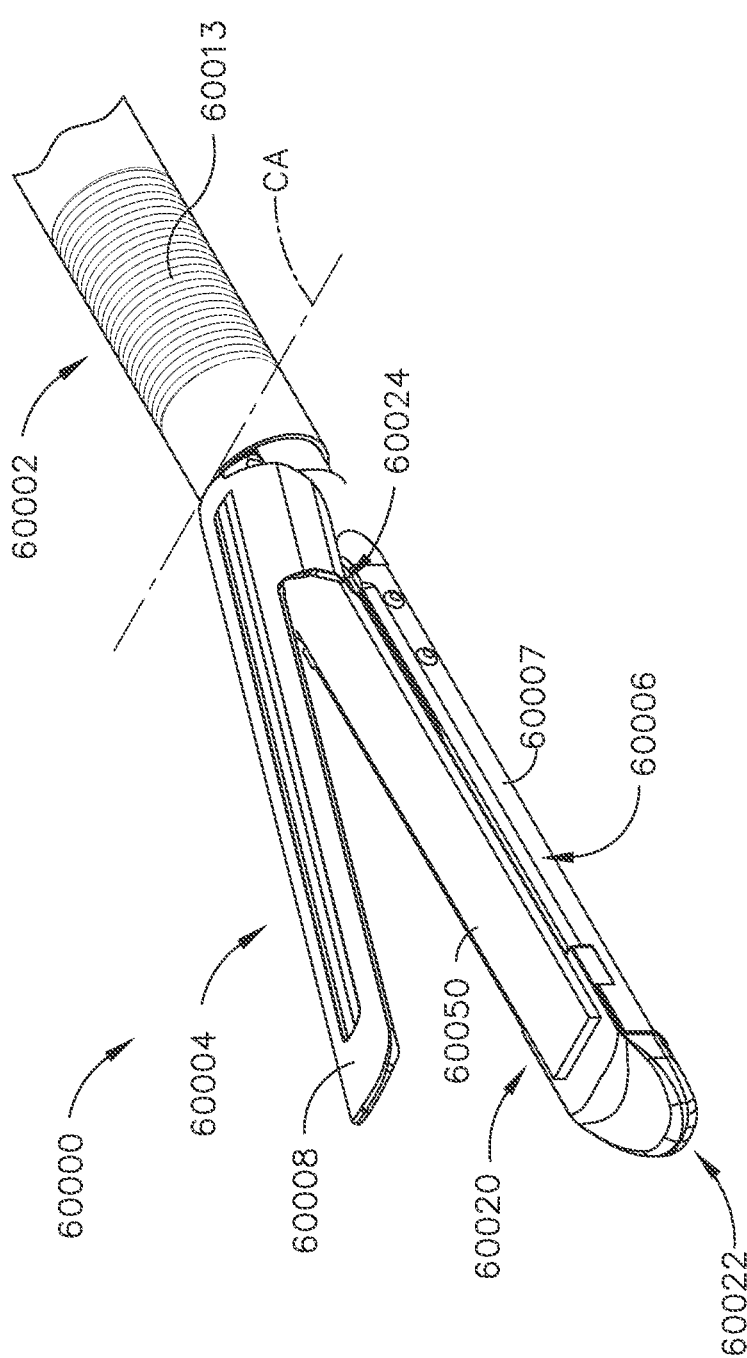
FIG. 1 is a partial perspective view of a surgical stapling system including an end effector.
Figure 2:
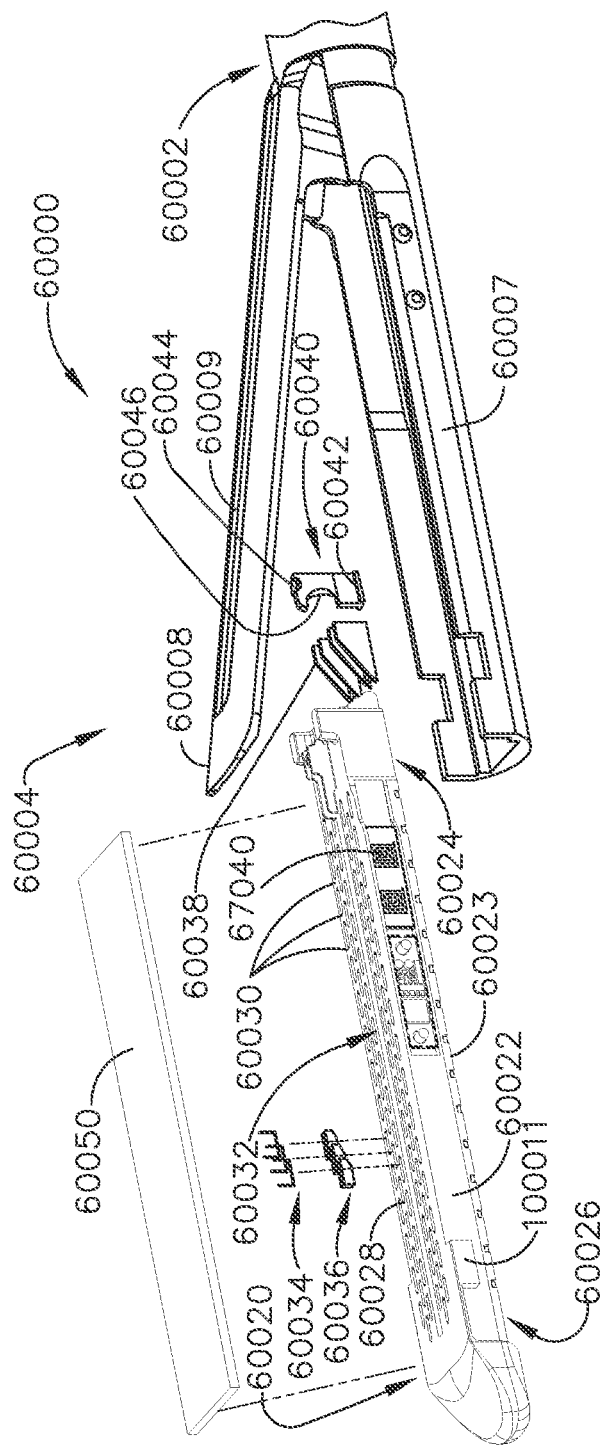
FIG. 2 is an exploded perspective view of the end effector of FIG. 1.

Applicant of the present application owns the following U.S. Patent Applications that were filed on Oct. 13, 2023 and which are each herein incorporated by reference in their respective entireties:

U.S. patent application Ser. No. 18/379,759, titled METHOD OF OPERATING A SURGICAL STAPLING INSTRUMENT;

U.S. patent application Ser. No. 18/379,762, titled SURGICAL STAPLING SYSTEMS WITH ADAPTIVE STAPLE FIRING ALGORITHMS;

U.S. patent application Ser. No. 18/379,763, titled LEARNED TRIGGERS FOR ADAPTIVE CONTROL OF SURGICAL STAPLING SYSTEMS;

U.S. patent application Ser. No. 18/379,766, titled CONTROL CIRCUIT FOR ACTUATING MOTORIZED FUNCTION OF SURGICAL STAPLING INSTRUMENT UTILIZING INERTIAL DRIVE TRAIN PROPERTIES;

U.S. patent application Ser. No. 18/379,768, titled PROPORTIONATE BALANCING OF THE FUNCTION IMPACT MAGNITUDE OF BATTERY OUTPUT TO PEAK MOTOR CURRENT;

U.S. patent application Ser. No. 18/379,771, titled MOTOR OPTIMIZATION BY MINIMIZATION OF PARASITIC LOSSES AND TUNING MOTOR DRIVE CONFIGURATION;

U.S. patent application Ser. No. 18/379,773, titled APPARATUS AND METHOD TO REDUCE PARASITIC LOSSES OF THE ELECTRICAL SYSTEM OF A SURGICAL INSTRUMENT;

U.S. patent application Ser. No. 18/379,776, titled SURGICAL TOOL WITH RELAXED FLEX CIRCUIT ARTICULATION;

U.S. patent application Ser. No. 18/379,777, titled WIRING HARNESS FOR SMART STAPLER WITH MULTI AXIS ARTICULATION;

U.S. patent application Ser. No. 18/379,781, titled SURGICAL SYSTEM WITH WIRELESS ARRAY FOR POWER AND DATA TRANSFER;

U.S. patent application Ser. No. 18/379,784, titled SURGICAL STAPLE CARTRIDGE COMPRISING REPLACEABLE ELECTRONICS PACKAGE;

Applicant of the present application owns the following U.S. Patent Applications that were filed on Oct. 13, 2023 and which are each herein incorporated by reference in their respective entireties:

U.S. patent application Ser. No. 18/379,790, titled METHOD OF ASSEMBLING A STAPLE CARTRIDGE;

U.S. patent application Ser. No. 18/379,793, titled CONTROL SURFACES ON A STAPLE DRIVER OF A SURGICAL STAPLE CARTRIDGE;

U.S. patent application Ser. No. 18/379,796, titled INTEGRAL CARTRIDGE STIFFENING FEATURES TO REDUCE CARTRIDGE DEFLECTION;

U.S. patent application Ser. No. 18/379,801, titled STAPLE CARTRIDGE COMPRISING WALL STRUCTURES TO REDUCE CARTRIDGE DEFLECTION;

U.S. patent application Ser. No. 18/379,803, titled PANLESS STAPLE CARTRIDGE ASSEMBLY COMPRISING RETENTION FEATURES FOR HOLDING STAPLE DRIVERS AND SLED;

U.S. patent application Ser. No. 18/379,805, titled STAPLE CARTRIDGE COMPRISING A SLED HAVING A DRIVER LIFT CAM;

U.S. patent application Ser. No. 18/379,808, titled SURGICAL STAPLE CARTRIDGES WITH SLEDS CONFIGURED TO BE COUPLED TO A FIRING DRIVER OF A COMPATIBLE SURGICAL STAPLER;

U.S. patent application Ser. No. 18/379,810, titled STAPLE CARTRIDGE COMPRISING A COMPOSITE SLED;

U.S. patent application Ser. No. 18/379,811, titled SURGICAL INSTRUMENTS WITH JAW AND FIRING ACTUATOR LOCKOUT ARRANGEMENTS LOCATED PROXIMAL TO A JAW PIVOT LOCATION;

U.S. patent application Ser. No. 18/379,815, titled SURGICAL INSTRUMENTS WITH LATERALLY ENGAGEABLE LOCKING ARRANGEMENTS FOR LOCKING A FIRING ACTUATOR;

U.S. patent application Ser. No. 18/379,817, titled DUAL INDEPENDENT KEYED LOCKING MEMBERS ACTING ON THE SAME DRIVE MEMBER;

U.S. patent application Ser. No. 18/379,822, titled ADJUNCTS FOR USE WITH SURGICAL STAPLING INSTRUMENTS;

U.S. patent application Ser. No. 18/379,826, titled JAW CONTROL SURFACES ON A SURGICAL INSTRUMENT JAW;

U.S. patent application Ser. No. 18/379,827, titled ZONED ALGORITHM ADAPTIVE CHANGES BASED ON CORRELATION OF COOPERATIVE COMPRESSION CONTRIBUTIONS OF TISSUE;

U.S. patent application Ser. No. 18/379,831, titled STAPLE CARTRIDGES COMPRISING TRACE RETENTION FEATURES;

U.S. patent application Ser. No. 18/379,832, titled STAPLE CARTRIDGES COMPRISING STAPLE RETENTION FEATURES.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 2022, U.S. Pat. No. 10,898,183, entitled ROBOTIC SUR- GICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled Surgical fastener applying apparatus, which published on Sep. 1, 2016, U.S. Design Patent No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, a staple cartridge may not be removable from, or at least readily replaceable from, the first jaw. The second jaw comprises an anvil configured to deform staples ejected from the staple cartridge. The second jaw is pivotable relative to the first jaw about a closure axis; however, the first jaw may be pivotable relative to the second jaw. The surgical stapling system further comprises an articulation joint configured to permit the end effector to be rotated, or articulated, relative to the shaft. The end effector is rotatable about an articulation axis extending through the articulation joint. Alternatively, the surgical stapling system may not include an articulation joint.

The staple cartridge comprises a cartridge body. The cartridge body includes a proximal end, a distal end, and a deck extending between the proximal end and the distal end. In use, the staple cartridge is positioned on a first side of the tissue to be stapled and the anvil is positioned on a second side of the tissue. The anvil is moved toward the staple cartridge to compress and clamp the tissue against the deck. Thereafter, staples removably stored in the cartridge body can be deployed into the tissue. The cartridge body includes staple cavities defined therein wherein staples are removably stored in the staple cavities. The staple cavities are arranged in six longitudinal rows. Three rows of staple cavities are positioned on a first side of a longitudinal slot and three rows of staple cavities are positioned on a second side of the longitudinal slot. Other arrangements of staple cavities and staples may be possible.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions by a sled. The sled is movable between a proximal position adjacent the proximal end and a distal position adjacent the distal end. The sled comprises a plurality of ramped surfaces configured to slide under the drivers and lift the drivers, and the staples supported thereon, toward the anvil.

Further to the above, the sled is moved distally by a firing driver. The firing driver is configured to contact the sled and push the sled toward the distal end. The longitudinal slot defined in the cartridge body is configured to receive the firing driver. The anvil also includes a slot configured to receive the firing driver. The firing driver further comprises a first cam which engages the first jaw and a second cam which engages the second jaw. As the firing driver is advanced distally, the first cam and the second cam can control the distance, or tissue gap, between the deck of the staple cartridge and the anvil. The firing driver also comprises a knife configured to incise the tissue captured intermediate the staple cartridge and the anvil. It is desirable for the knife to be positioned at least partially proximal to the ramped surfaces such that the staples are ejected ahead of the knife.

Referring to FIG. 1, a surgical stapling system 60000 is shown. The surgical stapling system 60000 comprises a shaft 60002 and an end effector 60004 extending from the shaft 60002. The end effector 60004 comprises a first jaw 60006 and a second jaw 60008. The first jaw 60006 comprises an elongate channel 61007 and a staple cartridge 60020. The staple cartridge is configured to be replaced during a surgical procedure. Alternatively, the staple cartridge 60020 may not be removable from, or at least readily replaceable from, the first jaw 60006.

The second jaw 60008 comprises an anvil configured to deform staples ejected from the staple cartridge 60020. The second jaw 60008 is pivotable or otherwise movable relative to the first jaw 60006 about a closure axis CA between an open position and a closed position. The surgical stapling system 60000 further comprises an articulation joint 60013 configured to permit the end effector 60004 to be rotated, or articulated, relative to the shaft 60002. The end effector 60004 is rotatable about an articulation axis extending through the articulation joint. Alternatively, the surgical stapling system 60000 may not include an articulation joint.

The staple cartridge 60020 comprises a cartridge body 60022. The cartridge body includes a proximal end 60024, a distal end 60026, and a deck 60028 extending between the proximal end and the distal end. In use, the staple cartridge 60020 is positioned on a first side of the tissue to be stapled and the anvil 60008 is positioned on a second side of the tissue. The anvil 60008 is moved toward the staple cartridge 60020 to compress and clamp the tissue against the deck 60028. Thereafter, a plurality of staples 60034 that are removably stored in the cartridge body 60022 are deployed into the tissue. The staples 60034 are removably stored in corresponding staple cavities 60030 formed in the cartridge body 60022. The staple cavities 60030 are arranged in six longitudinal rows. Three rows of staple cavities 60030 are positioned on a first side of a longitudinal slot 60032 and three rows of staple cavities 60030 are positioned on a second side of the longitudinal slot 60032. Other arrangements of staple cavities and staples may be possible.

The staples 60034 are supported by staple drivers 60036 supported in the staple cavities 60030. Staples supported on staple drivers can be seen in U.S. Pat. No. 9,844,369, entitled, SURGICAL END EFFECTORS WITH FIRING ELEMENT MONITORING ARRANGEMENTS, the entire disclosure of which is hereby incorporated by reference herein. The drivers 60036 are movable between a first, or unfired position, and a second, or fired, position to eject the staples 60034 from the staple cavities 60030. The drivers 60036 are retained in the cartridge body by a retainer 60023 which extends around the bottom of the cartridge body 60022 and includes resilient members configured to grip the cartridge body and hold the retainer to the cartridge body. The drivers 60036 are movable between their unfired positions and their fired positions by a sled 60038. The sled 60038 is movable between a proximal position adjacent the proximal end 60024 of the cartridge body 60022 and a distal position adjacent the distal end 60026 of the cartridge body 60022. The sled 60038 comprises a plurality of ramped surfaces configured to slide under the drivers 60036 and lift the drivers, and the staples 60034 supported thereon, toward the anvil 60008.

Further to the above, the sled 60038 is moved distally by a firing actuator or firing member 60040. The firing actuator 60040 is configured to contact the sled 60038 and push the sled 60038 toward the distal end 60026. The longitudinal slot 60032 defined in the cartridge body 60022 is configured to receive the firing actuator 60040. The anvil 60008 also includes a slot 60009 configured to receive the firing actuator 60040. The firing actuator 60040 also comprises a knife 60046 configured to incise the tissue captured intermediate the staple cartridge 60020 and the anvil 60008.

Buttresses, tissue thickness compensators, and/or adjuncts (collectively referred to herein as "adjuncts") 60050 are often used to reinforce a staple line and provide support to the tissue surrounding the staple line. For example, an adjunct 60050 may be supported on the cartridge deck 60028. An adjunct, when used in connection with a replaceable staple cartridge, may be referred to herein as a "replaceable staple assembly", for example. In use, the end effector is positioned so as to capture the tissue to be stapled between the adjunct material and the underside of the anvil or the cartridge deck. Once the end effector has been properly positioned, the anvil is closed. The stapling instrument is then fired causing the firing actuator to move distally through the end effector. As the firing actuator moves distally, the firing actuator drives the sled or other camming arrangement into contact with the drivers in the staple cartridge that support the staples thereon. As the sled contacts the drivers, the drivers are driven toward the closed anvil driving the staples through the adjunct material and the clamped target tissue into forming contact with the underside of the anvil. The trailing knife on the firing actuator cuts through the stapled adjunct material and tissue until the firing actuator reaches the distal end of the staple cartridge and all of the staples stored therein have been fired. The anvil of the end effector is then opened and the stapled tissue is freed from the end effector. The adjunct material remains with the stapled tissue and eventually gets absorbed by the patient's body.

As discussed above, when a surgical procedure involves a long tissue cutline that requires use of multiple staple cartridges as well as corresponding multiple adjuncts, the subsequent adjunct is overlapped with a previously installed adjunct to form continuous lines of adjunct material on each side of the cut tissue throughout the length of the tissue cut line. When the knife of the firing actuator contacts the overlapped conventional adjuncts, the resistance created by overlapping material may cause the adjuncts to undesirably bunch, move or skew which might result in misalignment of the staples with the forming pockets in the anvil during firing and also may result in previously formed staples being cut through or otherwise damaged by the knife.

A staple cartridge 62000 configured to address the foregoing problem is illustrated in FIG. 5. The staple cartridge 62000 is configured to be seated in and removable from a first jaw as discussed above; however, a staple cartridge may not be removable from, or at least readily replaceable from, a first jaw. The staple cartridge 62000 comprises a cartridge body 62001 and a nose 62008. The cartridge body 62001 comprises a proximal end portion 62002, a distal end portion 62004, and a cartridge deck 62005 extending between the proximal end portion 62002 and the distal end portion 62004. The cartridge body 62001 also comprises a longitudinal slot 62006 which extends through the cartridge body 62001 from the proximal end portion 62002 to the distal end portion 62004. The cartridge body 62001 includes a plurality of first staple cavities 62010 and a plurality of second staple cavities 62012. Each staple cavity 62010, 62012 movably supports a corresponding staple driver therein. A corresponding staple is removably stored on the driver and is configured to be ejected out of the staple cavity 62010, 62012 by the driver during a firing stroke of the firing actuator.

As can be seen in FIG. 5, the first staple cavities 62010 are arranged in six longitudinal rows that extend from a location in the proximal end portion 62002 of the deck surface 62005 and extend distally to a distal end portion 62106 of the deck surface 62005. Three rows of first staple cavities 62010 are positioned on a first side of the longitudinal slot 62006 and three rows of first staple cavities 62010 are positioned on a second side of the longitudinal slot 62006. As can be seen in FIG. 5, each of the first staple cavities 62010 are parallel with or substantially parallel with the slot 62006. The first staple cavities 62010 in a second row 62015 are staggered relative to the first staple cavities 62010 in a first row 62013 of first staple cavities 62010 that is adjacent to the slot 62006. The first staple cavities 62010 in a third row 62017 are staggered relative to the first staple cavities 62010 in the second row 62015. Such arrangement results in overlapping staple lines.

Still referring to FIG. 5, the second staple cavities 62012 open through the distal portion 62016 of the deck surface 62005. As illustrated in FIG. 5, the second staple cavities 62012 are arranged in a different pattern than that of the first staple cavities 62010. The first staple cavities 62010 are positioned substantially parallel to the longitudinal slot 62006 whereas the second staple cavities 62012 are positioned at an angle with respect to the longitudinal slot 62006. The staple cavities 62012 can be positioned at an angle less than 90° with respect to the longitudinal slot 62006. For example, as shown in FIG. 5A, the longitudinal slot 62006 may define a slot axis SA and each second cavity 62012 may define a second cavity axis SPA. The second staple cavities 62012 can arranged in a line of two second staple cavities 62012 wherein each line is positioned so that the angle SCA between the slot axis SA and the second cavity axis SPA may be between 90° and 20°. Such angling of the second cavities 62012 relative to the longitudinal slot 62006 results in only two second staple cavities 62012 being provided in each line of second staple cavities. In the illustrated arrangement, four lines 62018A, 62018B, 62018C, and 62018D are employed on each side of the longitudinal sot 62006. Other numbers of lines of second cavities 62012 are contemplated.

Referring To FIGS. 6 and 7, there is shown a pair of angled staple drivers staple drivers 60037 that serve to support staples 60035 thereon in the second staple cavities 62012. As can be seen in those Figures, the staples 60035 are supported at angles SCA relative to the slot axis SA. The staple drivers 60037 are driven upwardly in their respective second staple cavities 62012 as the sled 60038 is driven distally during the firing stroke.

The staple cartridge 62000 differs from other staple cartridges that may employ entire lines staple cavities and staples that are biased at an angle relative to the longitudinal slot axis SA. The staple cartridge 62000 maintains the advantages provided by the three lines of parallel staples on each side of the longitudinal slot, but also gains an improved advantage provided by the few rows of second staple cavities and staples biased at an angle relative to the longitudinal slot and the axis of travel of the firing actuator. As discussed above, when completing multiple sequential firings, situations occur where the adjunct of a second firing stroke overlaps with the adjunct of a first firing stroke. As such, the overlap of adjuncts creates a certain thickness which makes cutting more difficult. This increase in cutting resistance can cause the second adjunct to bunch and skew which can divert the knife through some of the formed staples securing the distal end of the first adjunct material to the tissue. The angled pattern of the staples 60035 provides some relief by providing diversion paths for the knife during subsequent firings. For example, the angled pattern of the staples 60035 allows the knife to pass through a reinforced staple line more easily during a subsequent firing. The knife of subsequent firings can impact angled staples 60035 at a low angle which increases the probability that the knife will bounce off of the angled staples 60035 and pass by during the firing stroke instead of jamming and distorting the shape and formation of the angled staples 60035. As such, the position of the staple cavities 62012 and staples 60035 reduces the likelihood that the force of the knife through a previously fired staple line will impart damaging forces on the staples 60035 within the previously fired staple line. In addition, by providing the staples 60035 at an angle to the direction of travel of the firing actuator, the staples 60035 may provide an increased resistance to movement of the second adjunct material as the knife of the firing actuator initially contacts the second adjunct to cut and drive therethrough.

Figure 8:
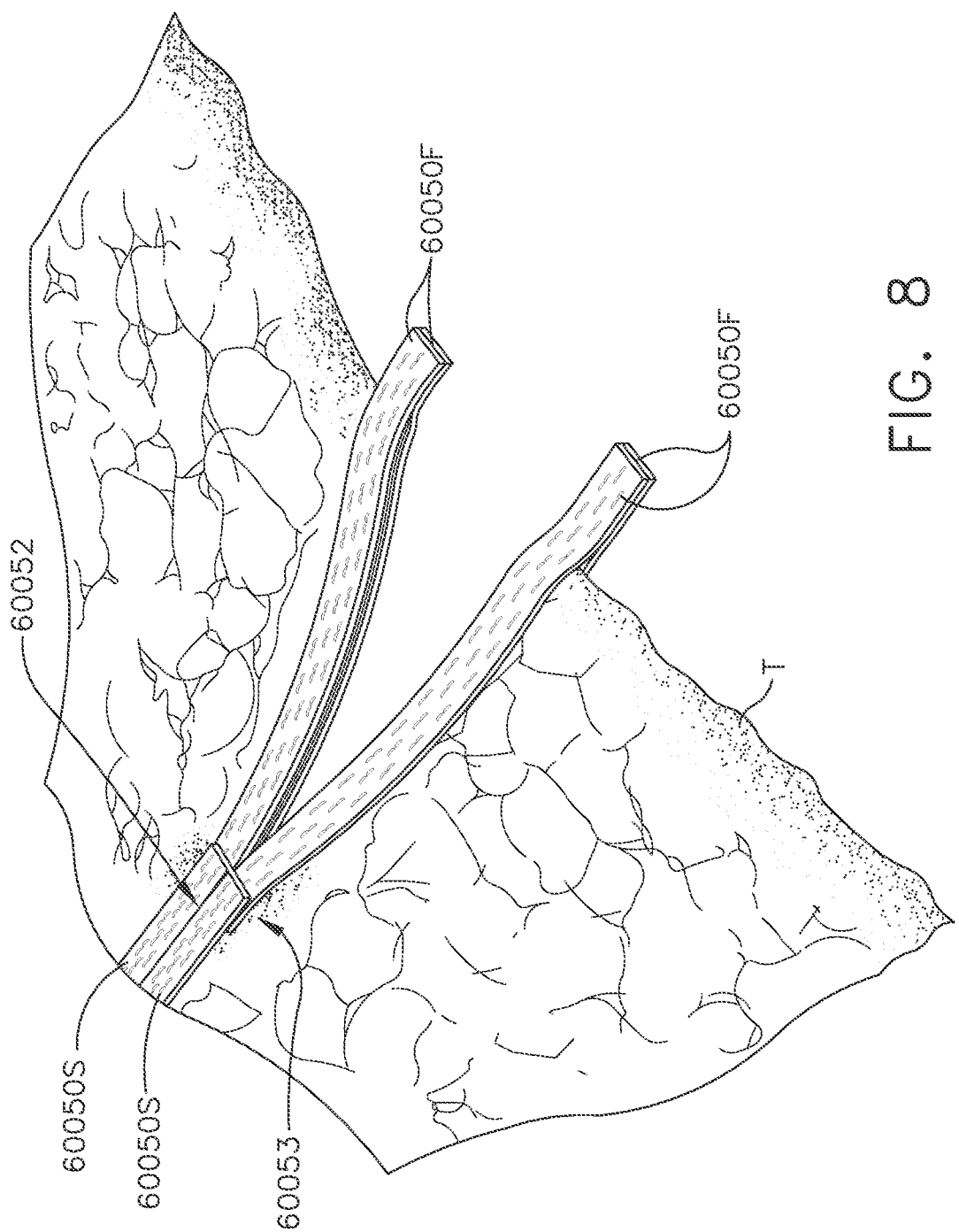
FIG. 8 is a perspective view of reinforced staple lines during subsequent staple firings.

FIG. 8 illustrates the use of staple cartridges 62000 to sequentially cut through tissue "T" when using a pair of first adjuncts 60050F and a pair of second adjuncts 60050S. The first adjuncts 60050F are stapled one both side of the tissue T using a first staple cartridge 62000 in the manners described herein. As such, one first adjunct 60050F is positioned on the cartridge deck and the other first adjunct 60050F is placed adjacent the underside of the anvil. The target tissue "T" is then positioned between the first adjuncts 60050F and then the anvil is closed and the firing actuator is fired. Once the first staple cartridge 62000 is fully fired and spent, it is removed from the end effector and replaced with another fresh staple cartridge 62000 as well as the pair of second adjuncts 60050S. The end effector is then positioned so that the proximal end portions 60051 of the second adjuncts 60050S overlap the distal end portions 60053 of the first adjuncts 60050F. The distal end portions 60053 of the first adjuncts 60050F were stapled with staples 60035 that were supported in the angled second cavities 62012 in the first staple cartridge 62000. The anvil of the end effector is then closed to capture the uncut tissue between the second adjuncts 60050S and the firing actuator is fired. As the firing actuator is moved distally, it contacts the four layers of overlapping adjuncts 60050F, 60050S which increases an amount of resistance experienced by the knife of the firing actuator. In the event that the adjuncts become skewed or bunched up, the angled orientation of the staples 60035 will increase the likelihood that the knife will bounce off staples 60035 and pass thereby without cutting through those previously formed staples. Alternative cartridge arrangements are contemplated wherein the second staple cavities 62012 (and staples 60035 supported thereon) are provided only in a proximal portion of the cartridge, and in other arrangements, the second staple cavities 62012 (and staples 60035 supported thereon) are provided only in a distal portion and a proximal portion. However, those angled cavities do not extend the entire length of the cartridge. A central segment of cavities comprising three lines of staple cavities that are parallel to each other and the slot axis can separate the proximal segment of angled cavities from the distal segment of angled cavities on both sides of the longitudinal slot.

The various adjuncts disclosed herein may be used in conjunction with the stapling system described above as well as other known stapler arrangements and systems to reinforce a staple line and provide support to the tissue surrounding the staple line. The adjunct arrangements discussed below may also address the problems outlined above by employing a change in the cross-section, pattern or integrity of the adjunct material to predefine locations wherein the adjunct material is configured to advantageously tear or separate. As such, the adjunct comprises a predefined and specific weakened portion or portions of the adjunct material to prevent a first adjunct from impacting the performance of a second adjunct during multiple sequential staple firings. Such weakened portion(s) comprise intermittent openings, and/or interruptions, and/or thinned out, tearable portions configured to tear during multiple sequential staple firings. The tearable portions are configured to enable the adjunct to shear in predefined ways. The tearable portions are also configured to enable the separation of specific staples from the adjunct upon the occurrence of dragging forces. By reducing the strength of certain portions of the adjunct, staple retaining or holding forces are reduced during a second cutting motion of the knife during multiple sequential staple firings.

Figure 9:
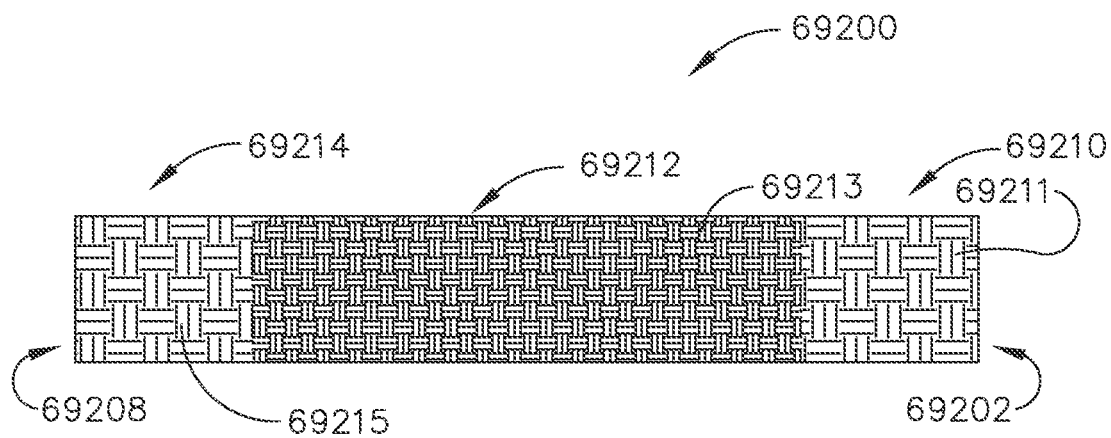
FIG. 9 is a top view of an adjunct for use with a staple cartridge and/or anvil in accordance with the present disclosure.
Figure 10:
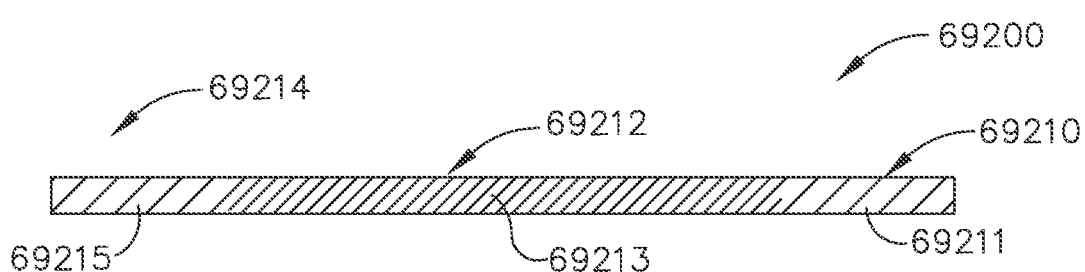
FIG. 10 is a cross-sectional side view of the adjunct of FIG. 9.

Turning to FIGS. 9 and 10, one adjunct 69200 of the present invention comprises a first region 69210, a second region 69212, and a third region 69214. The first region 69210 of the adjunct 69200 is located at the proximal end 69202 of the adjunct 69200. The third region 69214 is located at the distal end 69208 of the adjunct 69200. The second region 69212 is located in between the first region 69210 and the third region 69214. As seen in FIG. 9, the first region 69210 comprises a woven mesh 69211. The second region 69212 comprises a woven mesh 69213, and the third region 69214 comprises a woven mesh 69215. While the woven meshes 69211, 69213, 69215 may be formed from the same material (or different materials otherwise laminated or knitted together), the meshes 69211 and 69215 have attributes and strength characteristics that differ from the attributes of the woven mesh 69213. For example, all of the woven meshes 69211, 69213, and 69215 may comprise Vicryl® material or other woven materials disclosed herein. However, the material comprising the woven meshes 69211 and 69215 may have a different knot density, strand diameter, weave and/or denier, that differs from the knot density, strand diameter, weave and/or denier of the woven mesh 69213. The denier and/or number of strands forming the woven mesh 69213 may be higher than the denier and/or the number of stands forming the woven meshes 69211 and 69215. For example, the woven mesh 69213 may have 2×28 denier strands and the woven meshes 69211 and 69215 may have 1×28 denier strands, yet have the same weave pattern. The weave of the mesh materials 69211 and 69215 can be looser than the weave of the mesh material 69213. As can be seen in FIG. 10, while the compositions of the first region 69210 and the third region 69214 are the same, they differ from the composition of the second region 69212. However, in the illustrated example, the cross-sectional thicknesses of the regions 69210, 69212, and 69214 are the same. As such, the first and third regions 69210 and 69214 may be further weakened by exposing those portions (but not the second portion 69212) to one or more of moisture, ultraviolet light, and radiation (gamma, X-ray, E-beam, etc.) during manufacturing and prior to use.

In accordance with the present disclosure, the woven mesh 69213 comprises a greater strength than the woven meshes 69211 and 69215. This means that the woven mesh 69211 and woven mesh 69215 are easier to cut through and offer less resistance to the knife than the woven mesh 69213. In addition, the woven meshes 69211 and 69215 may be more likely to break free of the staples fired therethough should the adjunct material start to bunch or plow during firing. Thus, in applications wherein the first region 69210 of a second adjunct 69200 is overlapped over a third region 69214 of a previously-stapled, first adjunct 69200, the second adjunct 69200 is less likely to plow or bunch up when initially contacted by the knife. Further, in the event that second adjunct 69220 nonetheless starts to bunch or plow, the woven mesh 69215 forming the third region 69214 of the first adjunct 69200 is more likely to break away from the formed staples therein, leaving those staples fastened to the tissue. Likewise, the woven mesh 69211 forming the first region 69210 in the second adjunct 69200 is more likely to break away from any of the staples initially formed therein leaving those staples fastened to the underlying tissue. Thus, the various forms of adjunct 69200 serve to address the problems discussed above when using conventional adjuncts in sequential stapling and cutting applications.

Figure 11:
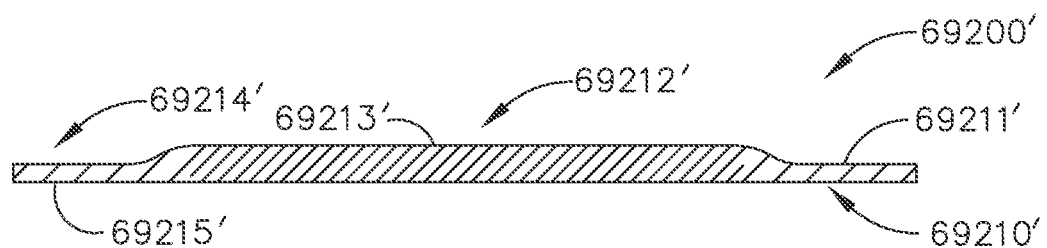
FIG. 11 is a cross-sectional side of an adjunct in accordance with the present disclosure.

Another adjunct 69200' is illustrated in FIG. 11. The adjunct 69200' comprises a first region 69210', a second region 69212', and a third region 69214'. The first region 69210', the second region 69212' and the third region 69214' may be similar to the first region 69210, the second region 69212, and the third region 69214, respectively described above. However, as can be seen in FIG. 11, the first region 69210' and the third region 69214' comprise equal thicknesses 69211' and 69215', respectively, whereas the second region 69212' comprises a different, or greater thickness 69213' than the thicknesses 69211' and 69215'. Alternatively, the adjunct 69200' can comprise further weakening the first and third regions 69210' and 69214' by exposing those portions (but not the second portion 69212) to one or more of moisture, ultraviolet light, and radiation (gamma, X-ray, E-beam, etc.) during manufacturing and prior to use. The adjunct 69200' is configured to provide similar benefits to that of the adjunct 69200 disclosed above.

Figure 12:
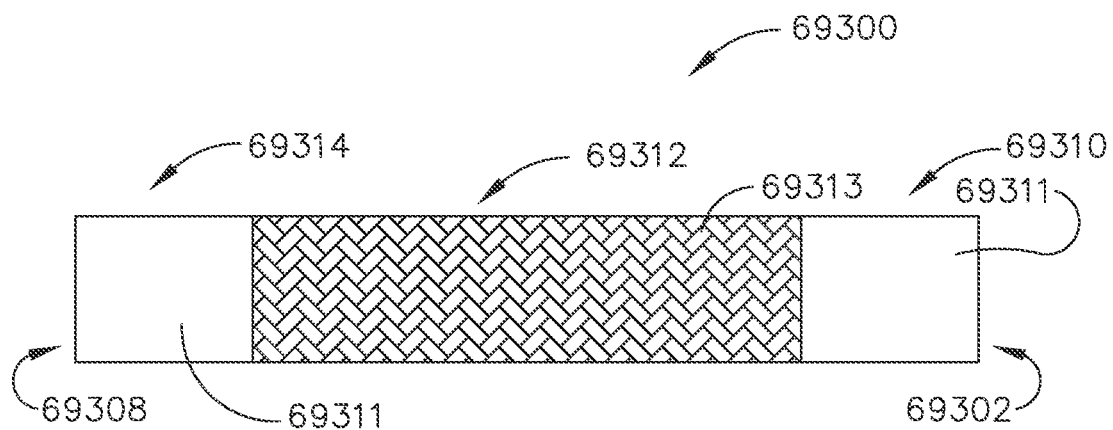
FIG. 12 is a top view of another adjunct for use with a staple cartridge and/or anvil in accordance with the present disclosure.
Figure 13:
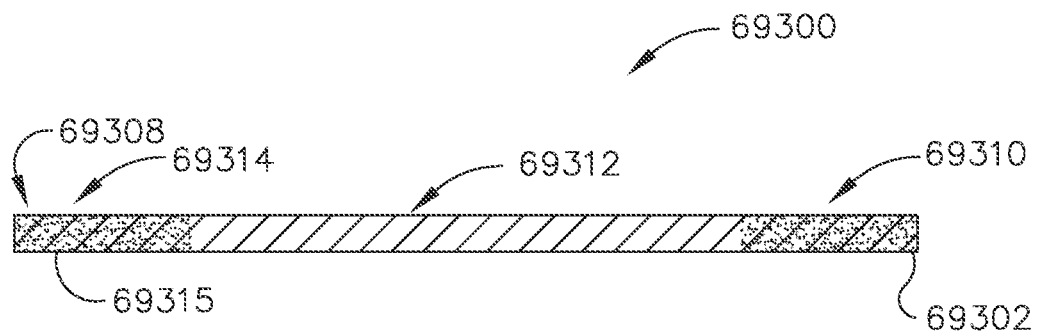
FIG. 13 is a cross-sectional side view of the adjunct of FIG. 12.

Turning to FIGS. 12 and 13, another adjunct 69300 of the present invention is disclosed. FIG. 13 is a cross-sectional side view of the adjunct 69300. The adjunct 69300 comprises a first region 69310, a second region 69312, and a third region 69314. The first region 69310 of the adjunct 69300 is located at the proximal end 69302 of the adjunct 69300. The third region 69314 is located at the distal end 69308 of the adjunct 69300. The second region 69312 is located between the first region 69310 and the third region 69314. As seen in FIG. 12, the third region 69312 comprises a woven mesh 69313 such as a woven Vicryl® material or any of the other woven materials disclosed herein. The first region 69310 and the second region 69314 comprise a non-woven material 69311 which may comprise any of the non-woven materials described below. The non-woven material 69311 is weaker than the woven material 69313 and provides less reinforcement to the staples formed therein. The material 69311 also provides less resistance to the knife as it is driven therethrough and thereby reduces the likelihood of plowing and bunching occurring during firing. Thus, in use, should the adjunct 69300 start to bunch or plow during cutting, the weaker first region 69310 and the weaker third region 69314 would be more likely to break away from the staples formed therein which may prevent those staples from being pulled out and/or damaged as the firing actuator passes therethrough. Alternatively, the adjunct 69300 can comprise further weakening the first and third regions 69310 and 69314 by exposing those portions (but not the second region 69312) to one or more of moisture, ultraviolet light, and radiation (gamma, X-ray, E-beam, etc.) during manufacturing and prior to use.

Figure 14:
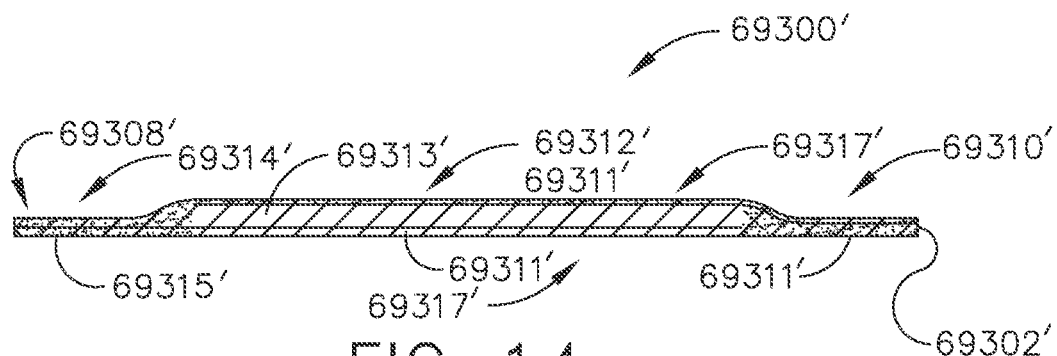
FIG. 14 is a cross-sectional side of an adjunct in accordance with the present disclosure.

FIG. 14 depicts another adjunct 69300' that is similar in many respects to the adjunct 69300 described above. As seen in FIG. 14, the adjunct 69300' comprises a first region 69310', a second region 69312', and a third region 69314'. The first region 69310' and the third region 69314' comprise cross-sectional thicknesses that differ from the cross-sectional thickness of the second region 69312'. In the illustrated arrangement, the cross-sectional thickness of the second region 69312' is greater than the cross-sectional thickness of the first region 69310' and the cross-sectional thickness of the third region 69314'. The second region 69312' may comprise a woven mesh 69313' such as a woven Vicryl® or other woven material disclosed herein. The first region 69310' and the third region 69314' comprise a non-woven material 69311' such as PDO, ORC, etc. described below. The non-woven material 69311' is weaker than the woven material 69313' and provides less reinforcement to the staples formed therein. In the illustrated arrangement, layers 69317' of the non-woven material 69311' are laminated on both sides of the woven material 69313'. As such, the second region 69312' comprises both materials 69313' and 69311'. However, the first region 69310' and the third region 69314' are comprised solely of the laminated layers of non-woven material 69311'. The woven material 69313' does not extend into the first region 69310' and the third region 69314'. The adjunct 69300' is configured to provide similar benefits to that of the adjunct 69300 disclosed above. Alternatively, the adjunct 69300' cab comprise further weakening the first and third regions 69310' and 69314' by exposing those portions (but not the second region 69312') to one or more of moisture, ultraviolet light, and radiation (gamma, X-ray, E-beam, etc.) during manufacturing and prior to use.

As discussed above, the differences in material composition can be accomplished by decreasing or increasing the knot density of the material, increasing or decreasing the strand diameter of the material, the denier, or using different materials in conjunction with one another. The first material may comprise a woven material such as Vicryl® or the like and extend the entire length of the adjunct. Layers of non-woven polymeric material of the types disclosed below may be laminated to the woven material. As such, the first material may be exposed to one or more of moisture, ultraviolet light, and radiation (gamma, X-ray, E-beam, etc.) prior to the lamination process. Alternatively, the entire adjunct may be exposed to one or more of moisture, ultraviolet light, and radiation (gamma, X-ray, E-beam, etc.) after the lamination process. In either case, the adjuncts are weakened to enable the knife to pass through the materials without causing bunching or plowing and to enable the adjunct to break away from formed staples if such bunching or plowing inadvertently occurs during firing.

Figure 15:
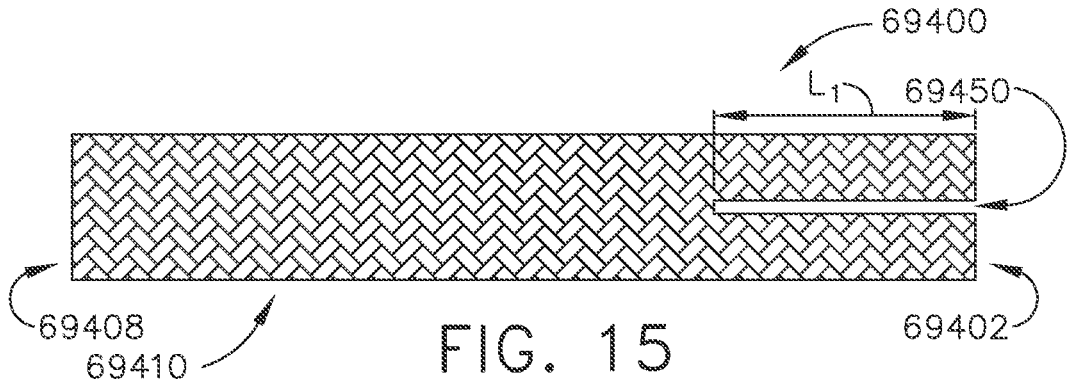
FIG. 15 is a top view of an adjunct for use with a staple cartridge and/or anvil in accordance with the present disclosure.

FIG. 15 depicts another adjunct 69400 that comprises a woven material 69410 of the various types and compositions disclosed herein. However, the adjunct 69400 may be fabricated from any of the other non-woven materials and compositions described herein. The adjunct comprises a proximal end 69402 and a distal end 69408. As can be seen in FIG. 15, a slot 69450 begins at a proximal end 69402 of the adjunct 69400 and extends a distance L1 into the adjunct 69450. As discussed above, when two adjuncts 69400 are used during sequential firing motions, the proximal end 69402 of a second adjunct 69400 will overlay the distal end 69408 of the first adjunct 69400. The slot 69450 provides a unique benefit of allowing for a knife to pass through the slot 69450 in the second adjunct 69400 where the two adjuncts 69400 overlap without encountering two layers of material thereby reducing the amount of resistance encountered by the knife in that region which might otherwise have led to moving, bunching or plowing of the second adjunct 69400. Thus, length L1 of the slot 69450 can be at least as long as the amount that a second adjunct 69400 is overlapped with a previously stapled adjunct to afford the knife unimpeded travel through the second adjunct 69400 in the area of adjunct overlap. The slot 69450 may be wide enough so that a knife of a surgical stapler and firing actuator may pass therethrough without contacting the adjunct material on the sides of the slot. In the illustrated arrangement, slot 69450 extends completely through the thickness of the adjunct material 69410 for the distance L1. The slot 69450 may only extend partially through the cross-sectional thickness of the adjunct material 69410 for the distance L1. Alternatively, the slot 69450 may comprise a slit. The slit may extend completely through the cross-sectional thickness of the adjunct material 69410 for the distance L1 or it may only extend partially through the cross-sectional thickness of the adjunct material 69410 for the distance L1. The slot 69450 is intended to eliminate or reduce the amount of resistance encountered by the knife as it passes through the proximal end of the adjunct 69400 (in the area of adjunct overlap).

Figure 16:
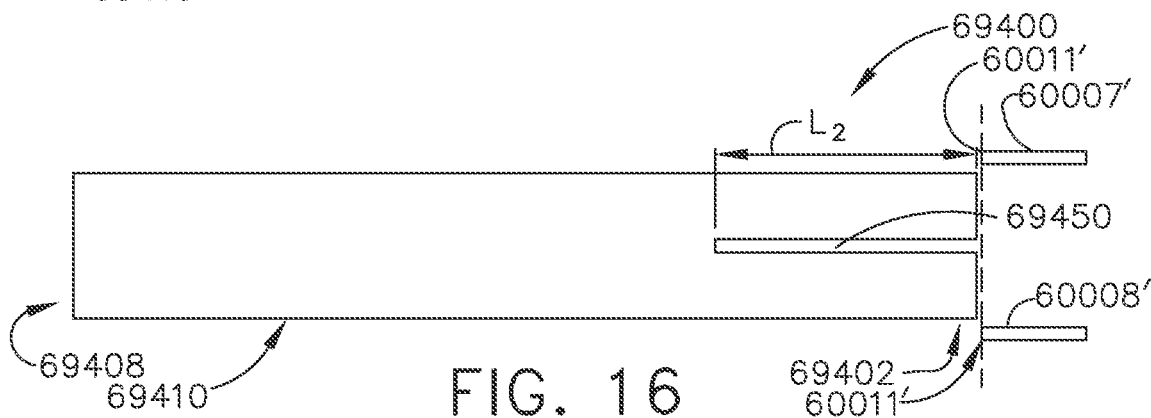
FIG. 16 is another top view of the adjunct of FIG. K15 in relation to tissue stops of a surgical staple anvil.

In various surgical procedures, to ensure that all of the tissue that is clamped between the jaws of the stapling instrument is stapled before being severed by the knife, the anvil of the stapler is commonly formed with "tissue stops" that prevent the tissue from extending proximally in the jaws beyond the proximal-most staples. FIG. 4 illustrates an anvil 60008' that has a pair of tissue stops 60009' formed on a proximal end portion thereof. Thus, when the anvil 60008' is in the open position and the target tissue is positioned between the anvil and the staple cartridge, the tissue contacts the distal edges 60011' of the tissue stops 60009' and is thereby prevented from being positioned any further proximally on the staple cartridge. However, the lines of staples extend proximally beyond that position so that those staples are fired prior to the knife contacting the tissue clamped in the jaws to ensure that the cut tissue is stapled. FIG. 16 illustrates positioning of the adjunct 69400 relative to the tissue stops 60009' of a surgical stapler. In such applications, to reduce the amount of resistance encountered by the knife as it passes through the adjunct 69400 and initially encounters the clamped tissue, it is desirable for the slot 69450 to extend distally past the tissue stops at least 5 mm (L2). This allows the knife to pass through the tissue unimpeded by the proximal end of the adjunct material 69450 to and allow for the firing of several staples through the proximal end of the adjunct 69400 before the knife starts to cut the adjunct material.

Figure 17:
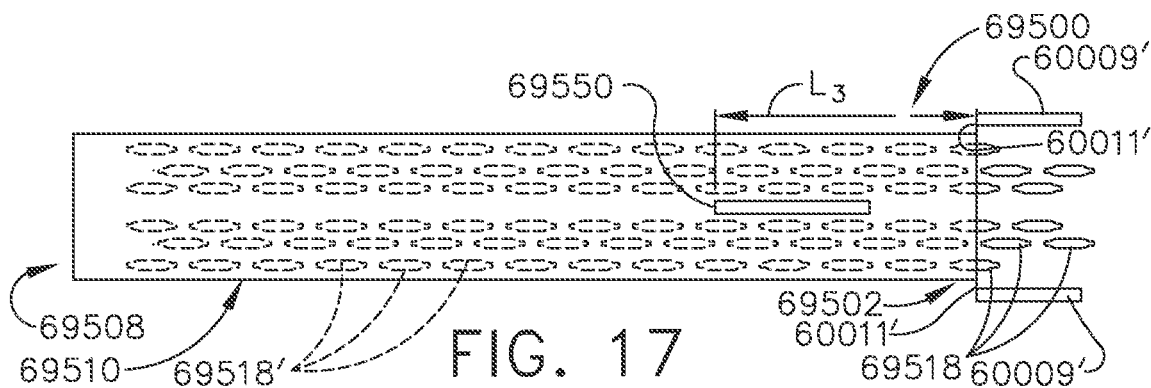
FIG. 17 is a top view of another adjunct for use with a staple cartridge and/or anvil in accordance with the present disclosure, with staple pockets of a staple cartridge shown in phantom lines for reference.

FIG. 17 illustrates an adjunct 69500 in accordance with the present disclosure. Adjunct 69500 comprises material 69510 that may comprise any of the adjunct composition and materials described herein. The adjunct 69500 comprises a proximal end 69502 and a distal end 69508. A slot 69550 is off set from the proximal end 69502 of the adjunct. Alternatively, the slot 69550 may extend through the proximal end 69502. The slot 69550 extends completely through the thickness of the adjunct material 69510. The slot 69550 may only extend partially through the cross-sectional thickness of the adjunct material 69510. Alternatively, the slot 69550 may comprise a slit. The slit may extend completely through the cross-sectional thickness of the adjunct material 69510 or it may only extend partially through the cross-sectional thickness of the adjunct material 69510. The slot 6950 is intended to reduce the amount of resistance encountered by the knife as it passes through the proximal end of the adjunct 69500 (in the area of likely adjunct overlap). FIG. 17 depicts the relationship of the adjunct 69500 relative to staple pockets 69518 of a staple cartridge in use. As can be seen in FIG. 17 several staple pockets 69518 are located proximal to the distal ends 60011' of the tissue stops 60009'. Distance L3 may be at least 5 mm as described above.

Figure 18:
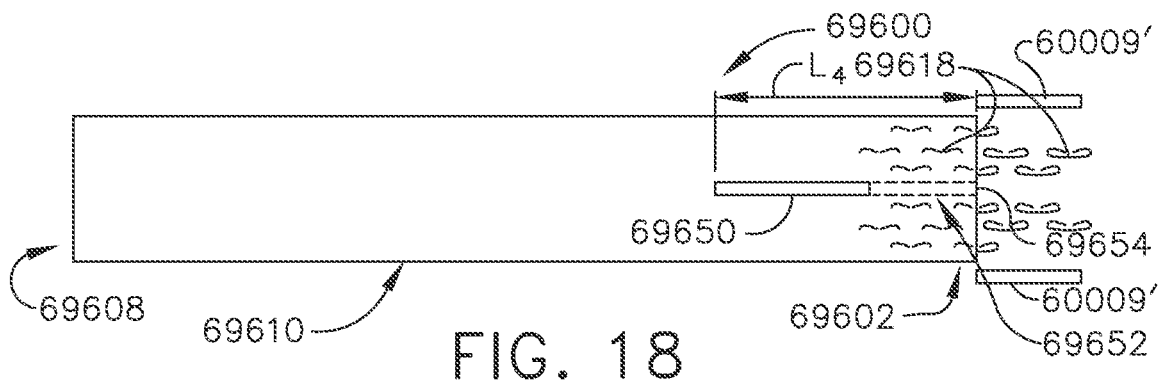
FIG. 18 is a top view of another adjunct for use with a staple cartridge and/or anvil in accordance with the present disclosure showing some formed staples from a staple cartridge for reference.

FIG. 18 illustrates another adjunct 69600 arrangement that may be fabricated from an adjunct material 69610 that may comprise any of the adjunct materials and arrangements described herein. The adjunct 69600 comprises a proximal end 69602 and a distal end 69608. As such, a slot 69650 extends a distance L3 from the proximal end of the adjunct 69600, but a proximal portion 69652 of the slot 69650 is filled with another adjunct non-woven material 69654 disclosed herein that will provide less resistance to the knife than the other material making up the adjunct 69600. For example, the adjunct material 69610 comprise a woven Vicryl® material with the proximal portion 69652 of the slot 69650 filled with an oxidized regenerated cellulose (ORC) or similar material 69554. FIG. 18 illustrates the position of the slot 69650 relative to some formed staples 69618 that were formed with an anvil employing tissue stops 60009'. The slot 69650 extends a distance L4 from the proximal end 69602. A distal end of the slot 69650 can be at least 5 mm from the ends 60011' of the tissue stops 60009'. Length L4 of the slot 69650 can be at least as long as the amount that a second adjunct 69600 is overlapped with a previously stapled adjunct to reduce resistance encountered by the knife as the knife travels through the area of adjunct overlap. Those of ordinary skill in the art will appreciate that any of the foregoing slot/slit arrangements may be employed with any one of the adjunct configurations.

Figure 19:
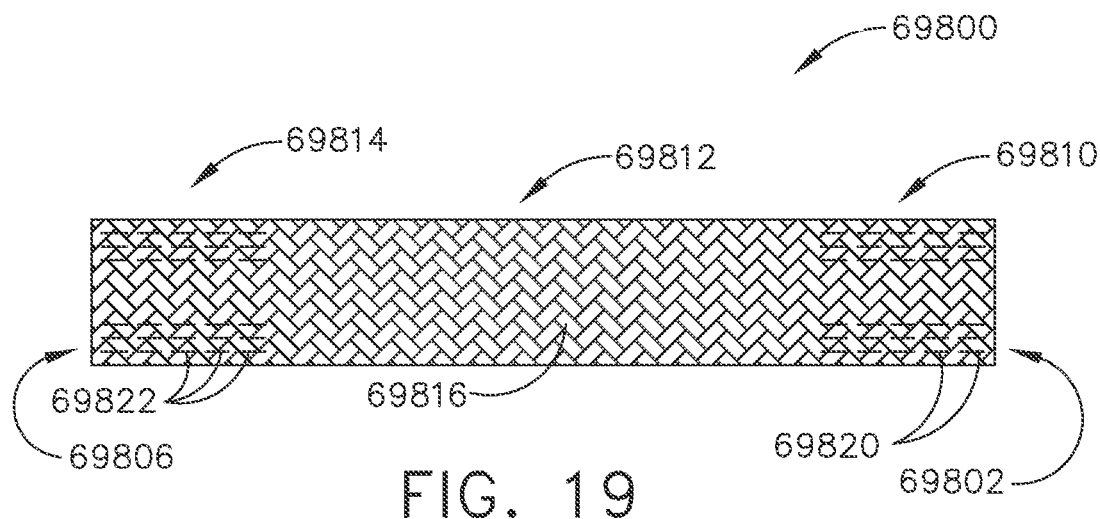
FIG. 19 is a top view of another adjunct for use with a staple cartridge and/or anvil in accordance with the present disclosure.

FIG. 19 depicts an adjunct 69800 that is similar to the adjuncts 69200, 69200' 69300, and 69300'. The adjunct 69800 comprises a woven material 69816 of the various types and constructions described herein, however the adjunct 69800 may comprise any of the non-woven adjunct materials and arrangements described herein. As can be seen in FIG. 19, the adjunct 69800 comprises a series of proximal perforations or cut out portions 69820 provided adjacent the proximal end 69802 to define a proximal weakened portion 69810 and a series of distal perforations or cut out portions 69822 adjacent a distal end 69606 to define a distal weakened portion 69814. No perforations are provided in a central portion 69812 extending between the proximal weakened portion 69810 and the distal weakened portion 69814. In use, should the adjunct 69800 start to bunch or plow during cutting, the proximal weakened portion 69810 and the distal weakened portion 69814 enable those portions to break away from the staples formed therein which may prevent those staples from being pulled out and/or damaged as the firing actuator passes therethrough. Those of ordinary skill in the art will appreciate that any of the foregoing perforation/cut out arrangements may be employed with any one of the adjunct configurations, including those adjuncts employing a slot or slit. In addition to the perforations and cutout portions, the weakened proximal portion 69810 and the weakened distal portion 69814 (but not the center portion 69812) may be exposed to one or more of moisture, ultraviolet light, and radiation (gamma, X-ray, E-beam, etc.) during manufacturing and prior to use.

Figure 20:
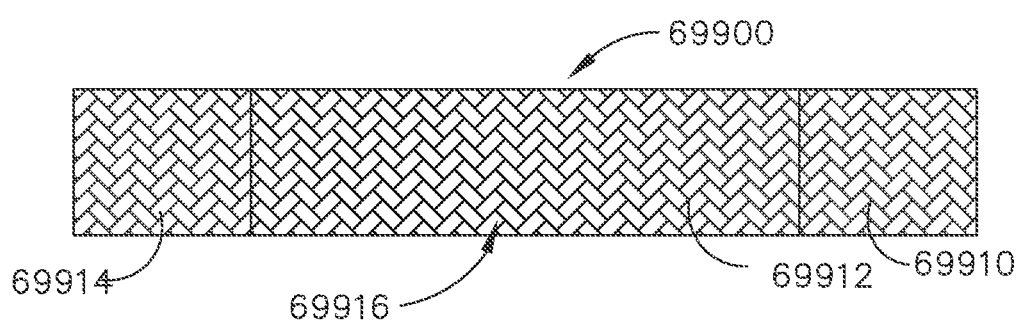
FIG. 20 is a top view of another adjunct for use with a staple cartridge and/or anvil in accordance with the present disclosure.

FIG. 20 illustrates another adjunct 69900 that comprises a woven material 69916. The adjunct 69900 can comprise a weakened proximal portion 69910 and a weakened distal portion 69914 which provide the above-discussed advantages. The weakened portions 69910 and 69914 are formed by exposing those portions (but not a center portion 69912) to one or more of moisture, ultraviolet light, and radiation (gamma, X-ray, E-beam, etc.) during manufacturing and prior to use. Alternatively, the adjunct 69900 may comprise any of the various adjunct materials described herein with the weakened proximal portion 69910 and the weakened distal portion 69914 being created by exposing those portions of the adjunct to one or more of moisture, ultraviolet light, and radiation (gamma, X-ray, E-beam, etc.) during manufacturing and prior to use.

Figure 21:
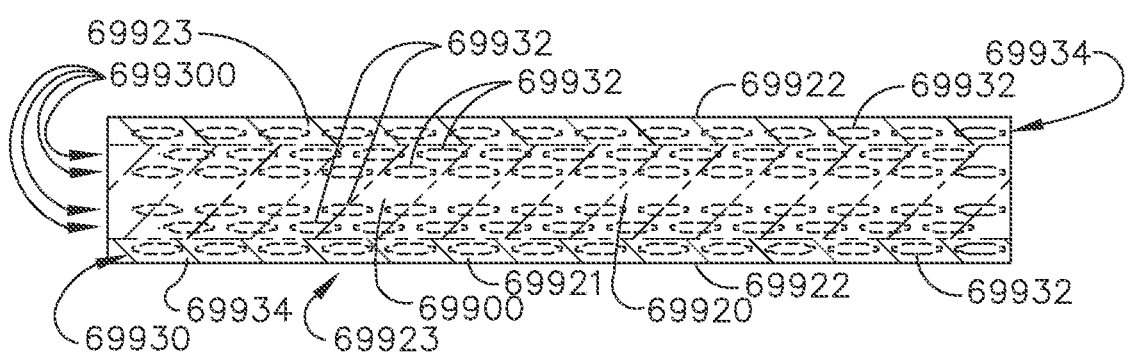
FIG. 21 is a top view of another adjunct for use with a staple cartridge and/or anvil in accordance with the present disclosure.
Figure 22:
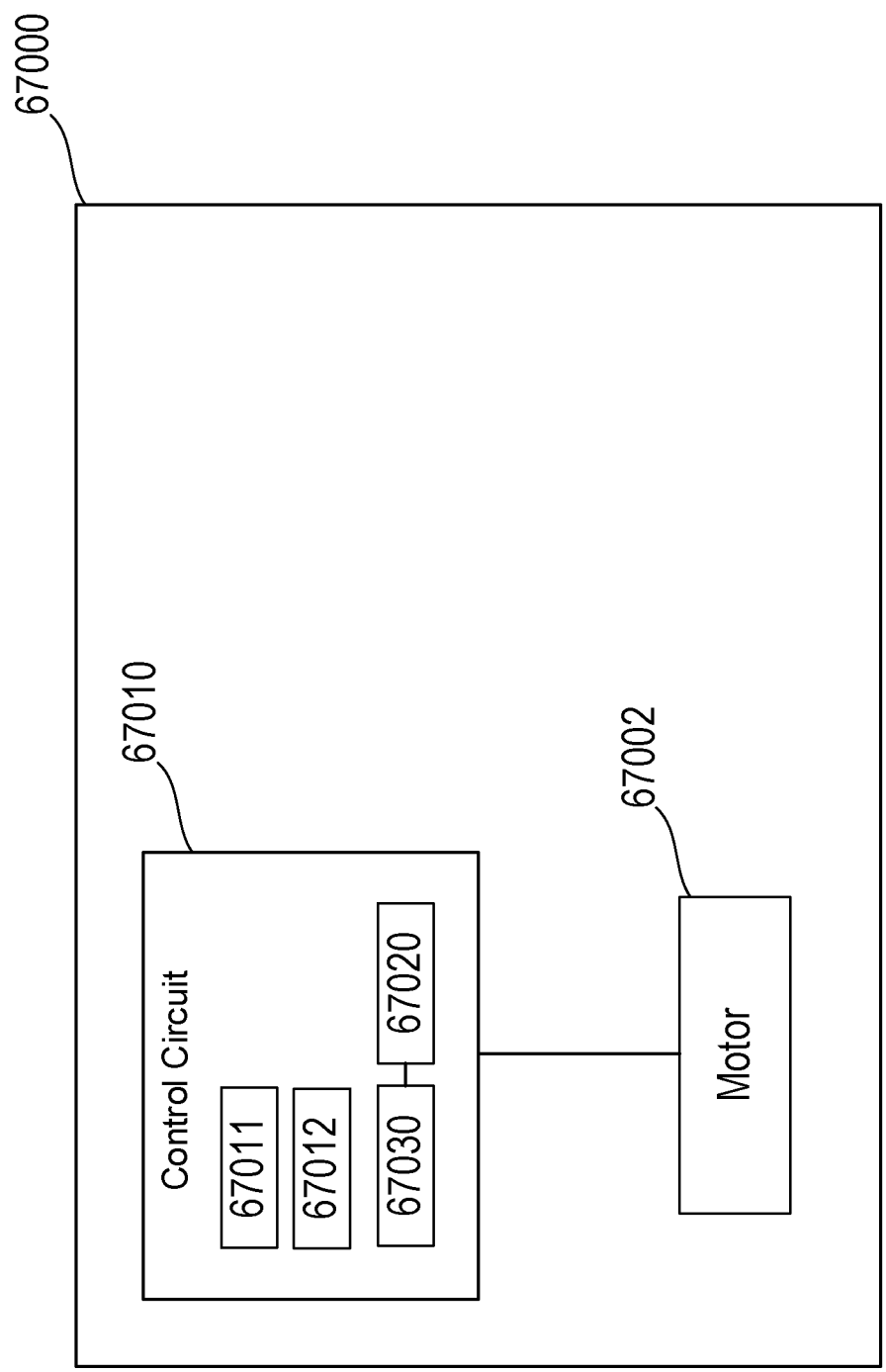
FIG. 22 is a diagram of a control system in accordance with the present disclosure.

FIG. 21 illustrates another adjunct 69900' that comprises a central region 69920 that corresponds to two central rows 69930 of staple pockets 69932 (shown in phantom) on each side of a longitudinal slot of a corresponding staple cartridge. The adjunct 69900' further comprises two lateral regions 69922 and 69924 that corresponds to the two outer rows 69934 of staple pockets 69932 in the staple cartridge. In the illustrated arrangement, the central region 69920 comprises a first material 69921 and the two lateral regions 69922 comprise a second material 69923 that differs from the first material 69921. The first material 69921 comprises oxidized regenerated cellulose (ORC) or similar material and the second material comprises a woven material such as Vicryl® or similar material. The first material 69921 offers less resistance to cutting than does the second material 69923 which provides added strength to the outer rows of staples. Other materials described herein may be employed wherein the first material 69921 is weaker (offers less resistance to knife travel and/or is more likely to break away from formed staples should the adjunct start bunching or plowing) than the second material.

The entire adjunct 69900' can be degraded during manufacturing by exposing the adjunct 69000' to one or more of moisture, ultraviolet light, and radiation (gamma, X-ray, E-beam, etc.) during manufacturing and prior to use. This will further weaken the adjunct 69900' and reduce the resistivity to cutting (and plowing) and enhance the ability to breaking away from formed staples should plowing occur during firing. The first material 69921 and/or the second material 69923 may be degraded by exposure to one or more of moisture, ultraviolet light, and radiation (gamma, X-ray, E-beam, etc.) prior to being laminated or otherwise attached together to form the adjunct 69900'.

In addition to the various attributes described above, any of the adjuncts described herein may comprise materials characterized by one or more of the following properties: biocompatible, bioabsorable, bioresorbable, biodurable, biodegradable, compressible, fluid absorbable, swellable, self-expandable, bioactive, medicament, pharmaceutically active, anti-adhesion, haemostatic, antibiotic, anti-microbial, anti-viral, nutritional, adhesive, permeable, hydrophilic and/or hydrophobic, for example. In still other configurations, the adjunct may comprise at least one of a haemostatic agent, such as fibrin and thrombin, an antibiotic, such as doxycpl, and medicament, such as matrix metalloproteinases (MMPs).

The adjuncts described herein may comprise synthetic and/or non-synthetic materials. For example, the adjunct may comprise a polymeric composition comprising one or more synthetic polymers and/or one or more non-synthetic polymers. The synthetic polymer may comprise a synthetic absorbable polymer and/or a synthetic non-absorbable polymer. The polymeric composition comprises a biocompatible foam, for example. The biocompatible foam may comprise a porous, open cell foam and/or a porous, closed cell foam, for example. The biocompatible foam may have a uniform pore morphology or may have a gradient pore morphology (i.e. small pores gradually increasing in size to large pores across the thickness of the foam in one direction). The polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the adjunct may comprise a foam reinforced by a filamentous matrix or may comprise a foam having an additional hydrogel layer that expands in the presence of bodily fluids to further provide the compression on the tissue. An adjunct described herein could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. The adjunct may comprise a microgel or a nanogel. The hydrogel may comprise carbohydrate-derived microgels and/or nanogels. An adjunct described herein may be reinforced with fibrous non-woven materials or fibrous mesh type elements, for example, that can provide additional flexibility, stiffness, and/or strength. An adjunct that has a porous morphology which exhibits a gradient structure such as, for example, small pores on one surface and larger pores on the other surface can be employed. Such morphology could be more optimal for tissue in-growth or haemostatic behavior. Further, the gradient could be also compositional with a varying bio-absorption profile. A short term absorption profile may be preferred to address hemostasis while a long term absorption profile may address better tissue healing without leakages, for example.

Examples of non-synthetic materials that may comprise any of the adjuncts described herein include, but are not limited to, lyophilized polysaccharide, glycoprotein, bovine pericardium, collagen, gelatin, fibrin, fibrinogen, elastin, proteoglycan, keratin, albumin, hydroxyethyl cellulose, cellulose, oxidized cellulose, oxidized regenerated cellulose (ORC), hydroxypropyl cellulose, carboxyethyl cellulose, carboxymethylcellulose, chitan, chitosan, casein, alginate, and combinations thereof.

Examples of synthetic absorbable materials that may comprise any of the adjuncts disclosed herein include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and -trimethylene carbonate, poly(glycerol sebacate) (PGS), poly(dioxanone) (PDS), polyesters, poly(orthoesters), polyoxaesters, polyetheresters, polycarbonates, polyamide esters, polyanhydrides, polysaccharides, poly(ester-amides), tyrosine-based polyarylates, polyamines, tyrosine-based polyiminocarbonates, tyrosine-based polycarbonates, poly(D,L-lactide-urethane), poly(hydroxybutyrate), poly(B-hydroxybutyrate), poly(E-caprolactone), polyethyleneglycol (PEG), poly[bis(carboxylatophenoxy)phosphazene]poly(amino acids), pseudo-poly(amino acids), absorbable polyurethanes, poly(phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, and combinations thereof. The polyester may be selected from the group consisting of polylactides, polyglycolides, trimethylene carbonates, polydioxanones, polycaprolactones, polybutesters, and combinations thereof.

Any of the adjuncts described herein may comprise a surfactant. Examples of surfactants may include, but are not limited to, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers.

The polymeric composition can comprise a pharmaceutically active agent. The polymeric composition may release a therapeutically effective amount of the pharmaceutically active agent. The pharmaceutically active agent may be released as the polymeric composition is desorbed/absorbed. The pharmaceutically active agent may be released into fluid, such as, for example, blood, passing over or through the polymeric composition. Examples of pharmaceutically active agents may include, but are not limited to, haemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

The polymeric composition can comprise a haemostatic material. The haemostatic material may comprise poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, ¿-amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof. In one form, the adjunct is characterized by haemostatic properties.

As discussed herein, various surgical instruments comprise a motor control system 67000 configured to execute intelligent algorithms. The intelligent algorithms comprise sequences that are optimized to interact with physical features of an adjunct. The motor control system 67000 may detect the changes in the adjunct thickness and/or properties and adapt the firing stroke in response to the detected changes. The motor control system 67000 can change the firing speed and/or pause at locations in the adjunct if a different thickness and/or different properties are detected based on a predetermined initial threshold.

The motor control system 67000 comprises a control circuit 67010. The control circuit 67010 comprises a processor 67011 and a memory device 67012. The processor 67011 is in communication with the motor 67002 of the surgical instrument. The motor control system 67000 can include and/or receive data 67020 regarding the adjunct loaded in the instrument and adapt the firing stroke in response to the data 67020. The data 67020 can comprise a predetermined adjunct thickness threshold 67022. The data 67020 may be stored on a memory device 67030 within the control circuit 67010. The data 67020 may also be stored in or on the cartridge itself. The cartridge 60026 may comprise an RFID tag 67040 affixed thereto.

Figure 23:
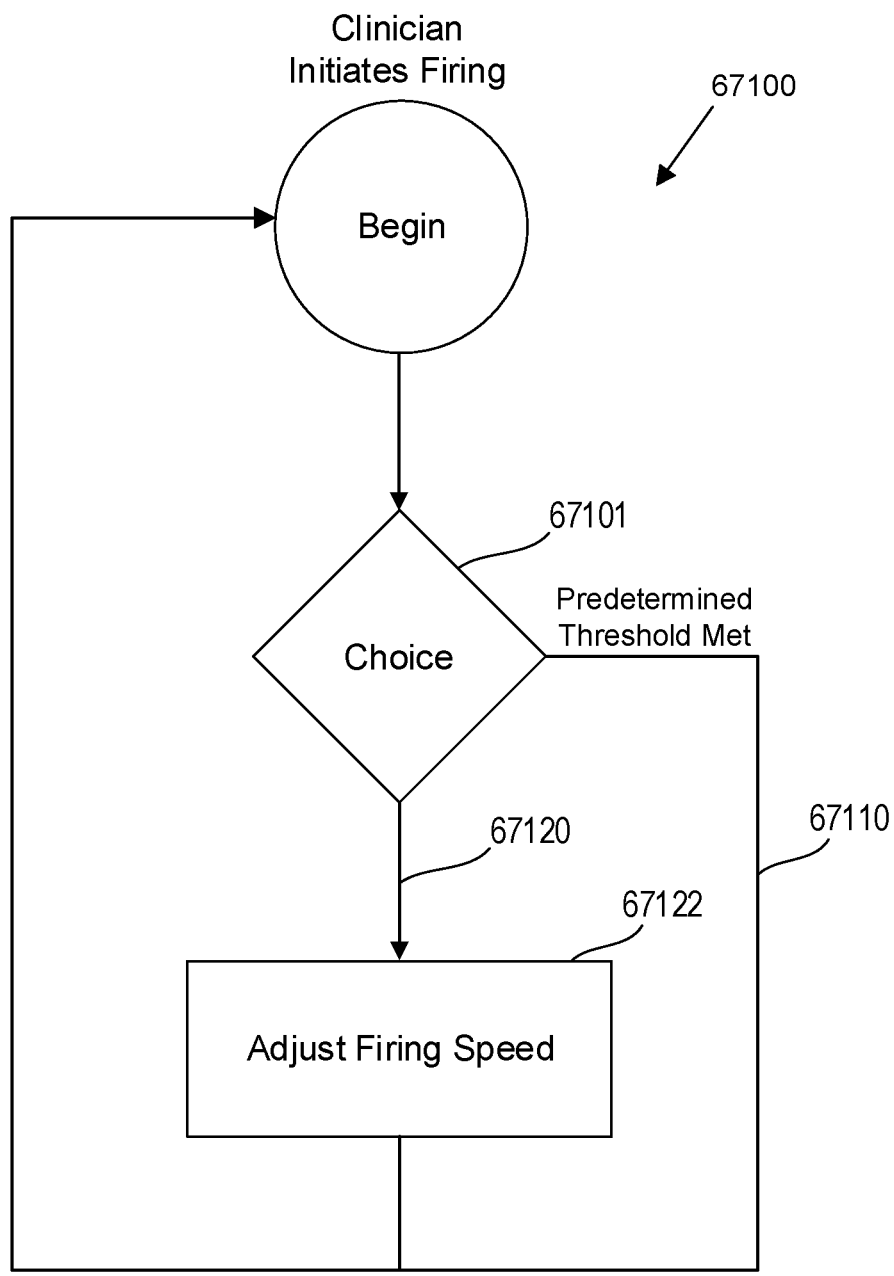
FIG. 23 is an algorithm configured for use with the control system of FIG. 22 in accordance with the present disclosure.

The surgical instruments described herein can comprise a control board, such as a printed control board (PCB), for example, which comprises the hardware and software for the motor control system 67000 of the surgical instruments. When the clinician initiates a firing motion, the firing member begins traveling distally through the cartridge which is detected by the motor control system 67000. At this point, the motor control system 67000 follows an algorithm 67100 for deciding when, or if, to adjust the firing speed. An algorithm 67100 is illustrated in FIG. 23 which can control this, although any suitable algorithm could be used.

As discussed above, the motor control system of a surgical instrument can comprise an intelligent algorithm 67100 which, according to predetermined criteria such as physical features of the adjunct, can change the firing speed or pauses the firing motion of the surgical instrument. As also discussed above, the algorithm can be configured to modify aspects of the firing motion of the surgical instrument based on the predetermined adjunct thickness threshold. As illustrated in FIG. 23, the algorithm 67100 comprises a step 67101 in which the motor control system 67000 assesses whether or not the physical features of the adjunct affixed to the staple cartridge aligns with the predetermined initial threshold. If it is determined at step 67101 that the physical features of the adjunct align with the predetermined initial threshold, the algorithm 67100 follows logic path 67110. In logic path 67110, the motor control system 67000 operates the surgical instrument at a consistent firing speed. Alternatively, if at step 67101 the motor control system 67000 determines that the physical features of the adjunct do not align with the predetermined initial threshold, the algorithm follows logic path 67120. In logic path 67120, the motor control system 67000 increases or decreases the speed of the firing motion at step 67122 to accommodate an adjunct that is thicker or thinner than the predetermined initial threshold, for example.

Further to the above, the motor control system 67000 of the surgical instrument 60000 comprises a pulse width modulation (PWM) control circuit configured to control the speed of the firing drive electric motor. The PWM control circuit applies voltage pulses to the firing drive electric motor to perform the staple firing stroke. The PWM control circuit can increase the duration of the voltage pulses it applies to the firing drive electric motor in order to increase the speed of the firing drive electric motor and, correspondingly, the speed of the staple firing stroke. The PWM control circuit can decrease the duration of the voltage pulses it applies to the firing drive electric motor in order to decrease the speed of the firing drive electric motor and, correspondingly, the speed of the staple firing stroke. In either event, the PWM control circuit can make these pulse length adjustments without substantially increasing or decreasing the magnitude of the voltage pulses being applied to the motor. That said, the magnitude of the voltage pulses, or certain voltage pulses, could be changed. In any event, as described in greater detail below, the control system is configured to drive the staple firing drive at a constant, or near constant, speed by adjusting the duration of the pulses via the PWM circuit. The entire disclosure of U.S. Pat. No. 8,499,992, entitled DEVICE AND METHOD FOR CONTROLLING COMPRESSION OF TISSUE, which issued on Aug. 6, 2013, is incorporated by reference herein.

The ratio of the time in which the voltage is applied to the electric motor (ON time) by the PWM circuit divided by the total time (ON time+OFF time) is the duty cycle of the staple firing drive motor. Thus, the duty cycle can range between 0% (completely OFF) and 100% (completely ON), i.e., a constant voltage without periodic interruptions. The terms ON and OFF suggest a non-zero voltage and a zero voltage; however, the terms ON and OFF are inclusive of HIGH and LOW voltages, respectively. The terms LOW or OFF include zero voltage and non-zero voltages that have a magnitude which is less than the HIGH or ON voltage. In view of the above, another way of expressing the duty cycle of the firing drive electric motor is the ratio of the time in which the voltage is applied to the electric motor (HIGH time) by the PWM circuit divided by the total time (HIGH time+LOW time).

The PWM control circuit applies the voltage pulses to the firing drive electric motor at regular intervals; however, the control system can comprise a frequency modulation (FM) control circuit to change the frequency of the voltage pulse intervals. The FM control circuit can decrease the interval between the voltage pulses to increase the speed of the firing drive electric motor and the staple firing stroke. Correspondingly, the FM control circuit increases the interval between the voltage pulses to decrease the speed of the firing drive electric motor and the staple firing stroke. In addition to or in lieu of the above, the control system can increase the magnitude of the voltage it applies to the firing drive electric motor to increase the speed of the firing drive electric motor and the staple firing stroke and/or decrease the magnitude of the voltage it applies to the firing drive electric motor to decrease the speed of the firing drive electric motor and the staple firing stroke.

The control system of the surgical instrument 60000 comprises an algorithm for controlling the speed of the staple firing member. The motor control system 67000 can included another algorithm configured to drive the staple firing member at a low speed, an intermediate speed, and a high speed. The low speed is 6 mm/s, or approximately 6 mm/s. The intermediate speed is 12 mm/s, or approximately 12 mm/s. The high speed is 20 mm/s, or approximately 20 mm/s. That said, the motor control system 67000 can be configured to operate the surgical instrument at any suitable number of speeds and/or at any suitable speed. The control system is configured to monitor the speed of the staple firing drive, via a motor speed sensor, and adjust the length of the voltage pulses applied to the electric motor of the staple firing drive to bring the speed of the staple firing drive to the target speed. For instance, if the target speed of the staple firing drive at a given point in the staple firing stroke is 12 mm/s and the actual speed is 11 mm/s, the control system increases the length of the voltage pulses it is applying to the electric motor to increase the speed of the staple firing drive. Stated another way, the control system increases the duty cycle of the firing drive electric motor to increase the speed of the staple firing drive. Correspondingly, the motor control system 67000 is configured to shorten the length of the voltage pulses it is applying to the firing drive electric motor if the speed of the staple firing drive exceeds the target speed until the speed of the staple firing drive reaches the target speed. Stated another way, the control system is configured to lower the duty cycle of the firing drive electric motor to decrease the speed of the staple firing drive. Notably, the target speed for the staple firing drive can change during the staple firing stroke. The entire disclosure of U.S. patent application Ser. No. 17/728,089, entitled STAPLING INSTRUMENT COMPRISING JAW MOUNTS, is incorporated by reference herein.

Various aspects of the subject matter described herein are set out in the following examples.

Example 1—An adjunct (69200, 69200', 69300, 69300', 69800, 69900) for use with a surgical stapling system (60000). The adjunct comprises a first region (69210, 69210', 69310, 69310', 69810, 69910) comprising a first composition, a second region (69212, 69212', 69312, 69312', 69812, 69912) distal to the first region, wherein the second region comprises a second composition, and a third region (69214, 69214', 69314, 69314', 69814, 69914) distal to the second region, wherein the third region comprises a third composition, and wherein the second composition differs from the first composition and the third composition.

Example 2—The adjunct of Example 1, further comprising a woven material (69816, 69916) spanning the first region, the second region, and the third region.

Example 3—The adjunct of Examples 1 or 2, wherein the first region comprises a first woven material (69211, 69211') comprising a first weave tightness, wherein the second region comprises a second woven material (69213, 69213') comprising a second weave tightness that is tighter than the first weave tightness, and wherein the third region comprises a third woven material (69215, 69215') that comprises the first weave tightness.

Example 4—The adjunct of Example 3, wherein the first woven material (69211, 69211') comprises a first denier, wherein the second woven material (69213, 69213') comprises a second denier that differs from the first denier, and wherein the third woven material (69215, 69215') comprises the first denier.

Example 5—The adjunct of Examples 3 or 4, wherein the first woven material (69211, 69211') comprises a first number of strands, wherein the second woven material (69213, 69213') comprises a second number of strands, and wherein the third woven material (69215, 69215') comprises the first number of strands.

Example 6—The adjunct of Example 5, wherein the second number of strands is greater than the first number of strands.

Example 7—The adjunct of Example 1, wherein the first region (69210, 69210', 69310, 69310') comprises a first material (69211, 69211'69311, 69311'), wherein the second region 69212, 69212', 69312, 69312') comprises a second material (69213, 69213', 69313, 69313') that differs from the first material, and wherein the third region (69214, 69214', 69314, 69314') comprises the first material.

Example 8—The adjunct of Example 7, wherein the first material comprises a non-woven material and wherein the second material comprises a woven material.

Example 9—The adjunct of Examples 1, 2, 3, 4, 5, 6, 7, or 8, wherein the first region extends from a proximal end of the adjunct, and wherein the adjunct comprises a slot (69450, 69550, 69650) extending longitudinally from the proximal end through at least a portion of the first region.

Example 10—The adjunct of Example 9, wherein said slot only extends partially through a cross-sectional thickness of the first region.

Example 11—The adjunct of Examples 9 or 10 wherein the slot comprises a slit.

Example 12—The adjunct of Examples 1, 2, 3, 4, 5, 6, 7, or 8, further comprising a plurality of perforations (6982) through the first region and another plurality of other perforations (69822) through the third region.

Example 13—The adjunct of Examples 1, 2, 3, 4, 5, 6, 7, 8, 9, 10, 11, 12, or 13 wherein the first region comprises a first cross-sectional thickness, wherein the second region comprises a second cross-sectional thickness that differs from the first cross-sectional thickness, and wherein the third region comprises the first cross-sectional thickness.

Example 14—The adjunct of Example 13, wherein the second cross-sectional thickness is greater than the first cross-sectional thickness.

Example 15—The adjunct of Examples 1, 2, 3, 4, 5, 6, 7, 8, 9, 10, 11, 12, 13, or 14 wherein the first region and the third region are exposed to at least one of moisture, ultraviolet light, and radiation prior to use.

Example 16—An adjunct for use with a surgical stapling system. The adjunct comprises a first region comprising a first composition, a second region distal to the first region, wherein the second region comprises a second composition, and third region distal to the second region, wherein the third region comprises a third composition, and wherein the second composition differs from the first composition and the third composition.

Example 17—The adjunct of Example 16, further comprising a woven material spanning the first region, the second region, and the third region.

Example 18—The adjunct of Example 17, wherein a first portion of the woven material spanning the first region comprises a first weave tightness, wherein a second portion of the woven material spanning the second region comprises a second weave tightness that is tighter than the first weave tightness, and wherein a third portion of the woven material spanning the third region comprises a third weave tightness that is the same as the first weave tightness.

Example 19—The adjunct of Example 18, wherein the first portion of the woven material comprises a first denier, wherein the second portion of the woven material comprises a second denier that differs from the first denier, and wherein the third portion of the woven material comprises a third denier that is the same as the first denier.

Example 20—The adjunct of Example 18, wherein the first portion of woven material comprises a first number of strands of the woven material, wherein the second portion of the woven material comprises a second number of strands of the woven material that differs from the first number of strands of the woven material, and wherein the third portion of the woven material comprises a third number of strands of the woven material that is the same as the first number of strands.

Example 21—The adjunct of Example 20, wherein the second number of strands of the woven material is greater than the first number of strands of the woven material.

Example 22—The adjunct of Example 16, wherein the first region comprises a first material, wherein the second region comprises a second material that differs from the first material, and wherein the third region comprises a third material that is the same as the first material.

Example 23—The adjunct of Example 22, wherein the first material comprises a non-woven material, and wherein the second material comprises a woven material.

Example 24—The adjunct of Example 16, wherein the first region extends from a proximal end of the adjunct, and wherein the adjunct comprises a slot extending longitudinally from the proximal end through at least a portion of the first region.

Example 25—The adjunct of Example 24, wherein said slot only extends partially through a cross-sectional thickness of the first region.

Example 26—The adjunct of Example 24, wherein the slot comprises a slit.

Example 27—The adjunct of Example 16, further comprising a plurality of perforations through the first region and another plurality of other perforations through the third region.

Example 28—The adjunct of Example 16, wherein the first region comprises a first cross-sectional thickness, wherein the second region comprises a second cross-sectional thickness that differs from the first cross-sectional thickness, and wherein the third region comprises a third cross-sectional thickness that is the same as the first cross-sectional thickness.

Example 29—The adjunct of Example 28, wherein the second cross-sectional thickness is greater than the first cross-sectional thickness.

Example 30—The adjunct of Example 16, wherein the first region and the third region are exposed to at least one of moisture, ultraviolet light, and radiation prior to use.

Example 31—An adjunct for use with a surgical stapling system. The adjunct comprising an elongate body comprising a proximal end, a distal end, and two lateral sides extending between the proximal end and the distal end. The elongate body further comprises a first material extending longitudinally through a central portion of the elongate body between the proximal end and the distal end, wherein the first material comprises a first composition, a length of second material extending longitudinally from the proximal end to the distal end between the first material and one of the lateral sides, wherein the second material comprises a second composition that differs from the first composition, and another length of the second material extending longitudinally from the proximal end to the distal end between the first material and another one of the lateral sides.

Example 32—The adjunct of Example 31, wherein the first material comprises a non-woven material, and wherein the second material comprises a woven material.

Example 33—A surgical stapling system comprising a staple cartridge. The staple cartridge comprises a cartridge body defining a proximal end and a distal end, an elongate slot extending from the proximal end toward the distal end, wherein the elongate slot defines a slot axis, a plurality of first staple cavities aligned in three lines of first staple cavities on each side of the elongate slot, wherein each line of first staple cavities is aligned on a corresponding first cavity axis that is parallel to the slot axis, and wherein each line of first staple cavities extend from the proximal end of the cartridge body to a position that is proximal to the distal end of the cartridge body, wherein each first staple cavity removably stores a corresponding first staple therein, and a plurality of second staple cavities formed on each side of the elongate slot in a distal portion of the cartridge body between the position that is proximal to the distal end and the distal end, wherein each second staple cavity is oriented on a second cavity axis that is arranged at angle relative to the slot axis, and wherein each second cavity removably stores a corresponding second staple therein.

Example 34—The surgical stapling system of Example 33, wherein the angle is between twenty degrees and ninety degrees.

Example 35—The surgical stapling system of Example 33, further comprising an adjunct supported on a deck surface of the cartridge body, wherein the adjunct comprises a first region comprising a first composition, a second region distal to the first region, wherein the second region comprises a second composition, and a third region distal to the second region, wherein the third region comprises a third composition, and wherein the second composition differs from the first composition and the third composition.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. patent application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one ore more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

It is worthy to note that any reference numbers included in the appended claims are used to reference exemplary embodiments/elements described in the present disclosure. Accordingly, any such reference numbers are not meant to limit the scope of the subject matter recited in the appended claims.

While this invention has been described as having exemplary designs, the present invention may be further modified within the spirit and scope of the disclosure. This application is therefore intended to cover any variations, uses, or adaptations of the invention using its general principles.

What is claimed is:

1. An adjunct for use with a surgical stapling system, wherein the adjunct comprises:
   a first region comprising a first composition;
   a second region distal to the first region, wherein the second region comprises a second composition; and
   a third region distal to the second region, wherein the third region comprises a third composition, wherein the second composition differs from the first composition and the third composition, and wherein the first region, the second region, and the third region are longitudinally aligned.

2. The adjunct of claim 1, further comprising a woven material spanning the first region, the second region, and the third region.

3. The adjunct of claim 2, wherein a first portion of the woven material spanning the first region comprises a first weave tightness, wherein a second portion of the woven material spanning the second region comprises a second weave tightness that is tighter than the first weave tightness, and wherein a third portion of the woven material spanning the third region comprises a third weave tightness that is the same as the first weave tightness.

4. The adjunct of claim 3, wherein the first portion of the woven material comprises a first denier, wherein the second portion of the woven material comprises a second denier that differs from the first denier, and wherein the third portion of the woven material comprises a third denier that is the same as the first denier.

5. The adjunct of claim 3, wherein the first portion of woven material comprises a first number of strands of the woven material, wherein the second portion of the woven material comprises a second number of strands of the woven material that differs from the first number of strands of the woven material, and wherein the third portion of the woven material comprises a third number of strands of the woven material that is the same as the first number of strands.

6. The adjunct of claim 5, wherein the second number of strands of the woven material is greater than the first number of strands of the woven material.

7. The adjunct of claim 1, wherein the first region comprises a first material, wherein the second region comprises a second material that differs from the first material, and wherein the third region comprises a third material that is the same as the first material.

8. The adjunct of claim 7, wherein the first material comprises a non-woven material, and wherein the second material comprises a woven material.

9. The adjunct of claim 1, further comprising a plurality of perforations through the first region and another plurality of other perforations through the third region.

10. An adjunct for use with a surgical stapling system, wherein the adjunct comprises:
    a first region comprising a first composition;
    a second region distal to the first region, wherein the second region comprises a second composition; and a third region distal to the second region, wherein the third region comprises a third composition, wherein the second composition differs from the first composition and the third composition, and wherein the first region extends from a proximal end of the adjunct, and wherein the adjunct comprises a slot extending longitudinally from the proximal end through at least a portion of the first region.

11. The adjunct of claim 10, wherein said slot only extends partially through a cross-sectional thickness of the first region.

12. The adjunct of claim 10, wherein the slot comprises a slit.

13. An adjunct for use with a surgical stapling system, wherein the adjunct comprises:
   a first region comprising a first composition;
   a second region distal to the first region, wherein the second region comprises a second composition; and
   a third region distal to the second region, wherein the third region comprises a third composition, wherein the second composition differs from the first composition and the third composition, wherein the first region comprises a first cross-sectional thickness, wherein the second region comprises a second cross-sectional thickness that differs from the first cross-sectional thickness, and wherein the third region comprises a third cross-sectional thickness that is the same as the first cross-sectional thickness.

14. The adjunct of claim 13, wherein the second cross-sectional thickness is greater than the first cross-sectional thickness.

15. An adjunct for use with a surgical stapling system, wherein the adjunct comprises:
   a first region comprising a first composition;
   a second region distal to the first region, wherein the second region comprises a second composition; and
   a third region distal to the second region, wherein the third region comprises a third composition, wherein the second composition differs from the first composition and the third composition, wherein the first region and the third region are exposed to at least one of moisture, ultraviolet light, and radiation prior to use.

16. An adjunct for use with a surgical stapling system, the adjunct comprising:
   an elongate body comprising a proximal end, a distal end, and two lateral sides extending between the proximal end and the distal end, wherein the elongate body further comprises:
      a first material extending longitudinally through a central portion of the elongate body between the proximal end and the distal end, wherein the first material comprises a first composition;
      a length of second material extending longitudinally from the proximal end to the distal end between the first material and one of the lateral sides, wherein the second material comprises a second composition that differs from the first composition; and
      another length of the second material extending longitudinally from the proximal end to the distal end between the first material and another one of the lateral sides.

17. The adjunct of claim 16, wherein the first material comprises a non-woven material, and wherein the second material comprises a woven material.

18. A surgical stapling system comprising:
   a staple cartridge, comprising:
   a cartridge body defining a proximal end and a distal end;
   an elongate slot extending from the proximal end toward the distal end, wherein the elongate slot defines a slot axis;
   a plurality of first staple cavities aligned in three lines of first staple cavities on each side of the elongate slot, wherein each line of first staple cavities is aligned on a corresponding first cavity axis that is parallel to the slot axis, and wherein each line of first staple cavities extend from the proximal end of the cartridge body to a position that is proximal to the distal end of the cartridge body, wherein each first staple cavity removably stores a corresponding first staple therein; and
   a plurality of second staple cavities formed on each side of the elongate slot in a distal portion of the cartridge body between the position that is proximal to the distal end and the distal end, wherein each second staple cavity is oriented on a second cavity axis that is arranged at angle relative to the slot axis, and wherein each second cavity removably stores a corresponding second staple therein.

19. The surgical stapling system of claim 18, wherein the angle is between twenty degrees and ninety degrees.

20. The surgical stapling system of claim 18, further comprising an adjunct supported on a deck surface of the cartridge body, wherein the adjunct comprises:
   a first region comprising a first composition;
   a second region distal to the first region, wherein the second region comprises a second composition; and
   a third region distal to the second region, wherein the third region comprises a third composition, and wherein the second composition differs from the first composition and the third composition.

* * * * *